(12) United States Patent
Matsuda et al.

(10) Patent No.: US 10,191,007 B2
(45) Date of Patent: Jan. 29, 2019

(54) SULFUR OXIDES DETECTION SYSTEM

(71) Applicant: TOYOTA JIDOSHA KABUSHIKI KAISHA, Toyota-shi, Aichi-ken (JP)

(72) Inventors: Kazuhisa Matsuda, Susono (JP); Kazuhiro Wakao, Susono (JP); Keiichiro Aoki, Shizuoka-ken (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 148 days.

(21) Appl. No.: 15/358,897

(22) Filed: Nov. 22, 2016

(65) Prior Publication Data

US 2017/0146480 A1 May 25, 2017

(30) Foreign Application Priority Data

Nov. 24, 2015 (JP) ............................... 2015-229173

(51) Int. Cl.
*G01N 27/407* (2006.01)
*G01N 27/406* (2006.01)
*G01M 15/10* (2006.01)
*G01N 27/417* (2006.01)
(Continued)

(52) U.S. Cl.
CPC ...... *G01N 27/4065* (2013.01); *G01M 15/104* (2013.01); *G01N 27/4072* (2013.01); *G01N 27/4074* (2013.01); *G01N 27/4076* (2013.01); *G01N 27/417* (2013.01);
(Continued)

(58) Field of Classification Search
CPC ............. G01N 27/406; G01N 27/4065; G01N 27/407; G01N 27/409; G01N 33/0042; F01N 2560/027
See application file for complete search history.

(56) References Cited

U.S. PATENT DOCUMENTS 5,857,324 A * 1/1999 Scappatura .......... B01D 53/922 60/274
9,753,005 B2 * 9/2017 Kato .................. G01N 27/4074
(Continued)

FOREIGN PATENT DOCUMENTS

| CN | 104919313 A | 9/2015 |
|----|-------------|--------|
| JP | H11-190721 A | 7/1999 |

(Continued)

*Primary Examiner* — Alexander S Noguerola
(74) *Attorney, Agent, or Firm* — Hunton Andrews Kurth LLP

(57) ABSTRACT

The sulfur oxides detection system includes a device part comprising a first electrochemical cell having a first solid electrolyte layer, a first electrode, and a second electrode; and a diffusion regulating layer. A power supply supplying voltage is provided between the electrodes as well as a detector detecting a first current correlation parameter, and a control part controlling the power supply and acquiring the first current correlation parameter. The control part controls the power supply so that a first voltage is applied between the electrodes and calculates a concentration of sulfur oxides in the measured gas based on the first current correlation parameter detected by the detector when the first voltage is applied between the electrodes, but it does not calculate the concentration of sulfur oxides in the measured gas when it judges that a concentration of water in the measured gas is not stable.

11 Claims, 16 Drawing Sheets

(51) Int. Cl.
    *G01N 27/419*     (2006.01)
    *G01N 33/00*     (2006.01)

(52) U.S. Cl.
    CPC ....... *G01N 27/419* (2013.01); *G01N 33/0042* (2013.01); *Y02A 50/248* (2018.01)

(56) References Cited

U.S. PATENT DOCUMENTS

| | | | |
|---|---|---|---|
| 2001/0008374 A1* | 7/2001 | Kataoka | G01N 27/123 324/120 |
| 2014/0353174 A1* | 12/2014 | Katayama | G01N 27/419 205/784 |
| 2015/0355136 A1 | 12/2015 | Kato et al. | |
| 2016/0061771 A1 | 3/2016 | Mizutani et al. | |

FOREIGN PATENT DOCUMENTS

| | | | | |
|---|---|---|---|---|
| JP | 2016-050879 A | 4/2016 | | |
| WO | WO 2014/112315 A1 * | 7/2014 | ............. | G01N 27/41 |

* cited by examiner

FIG. 1
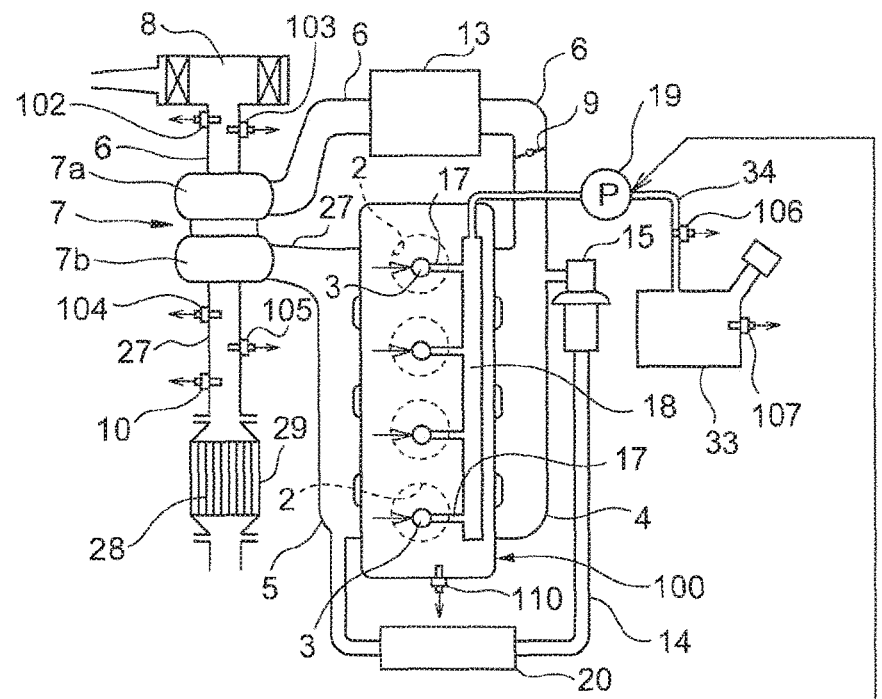
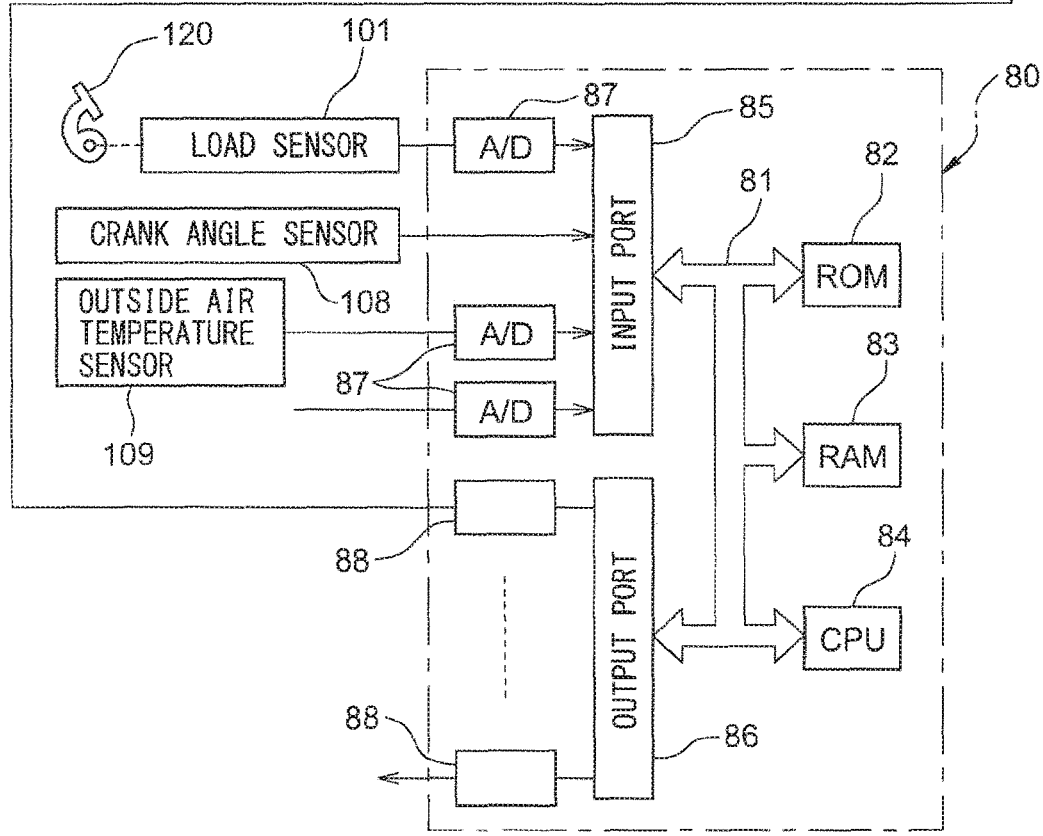

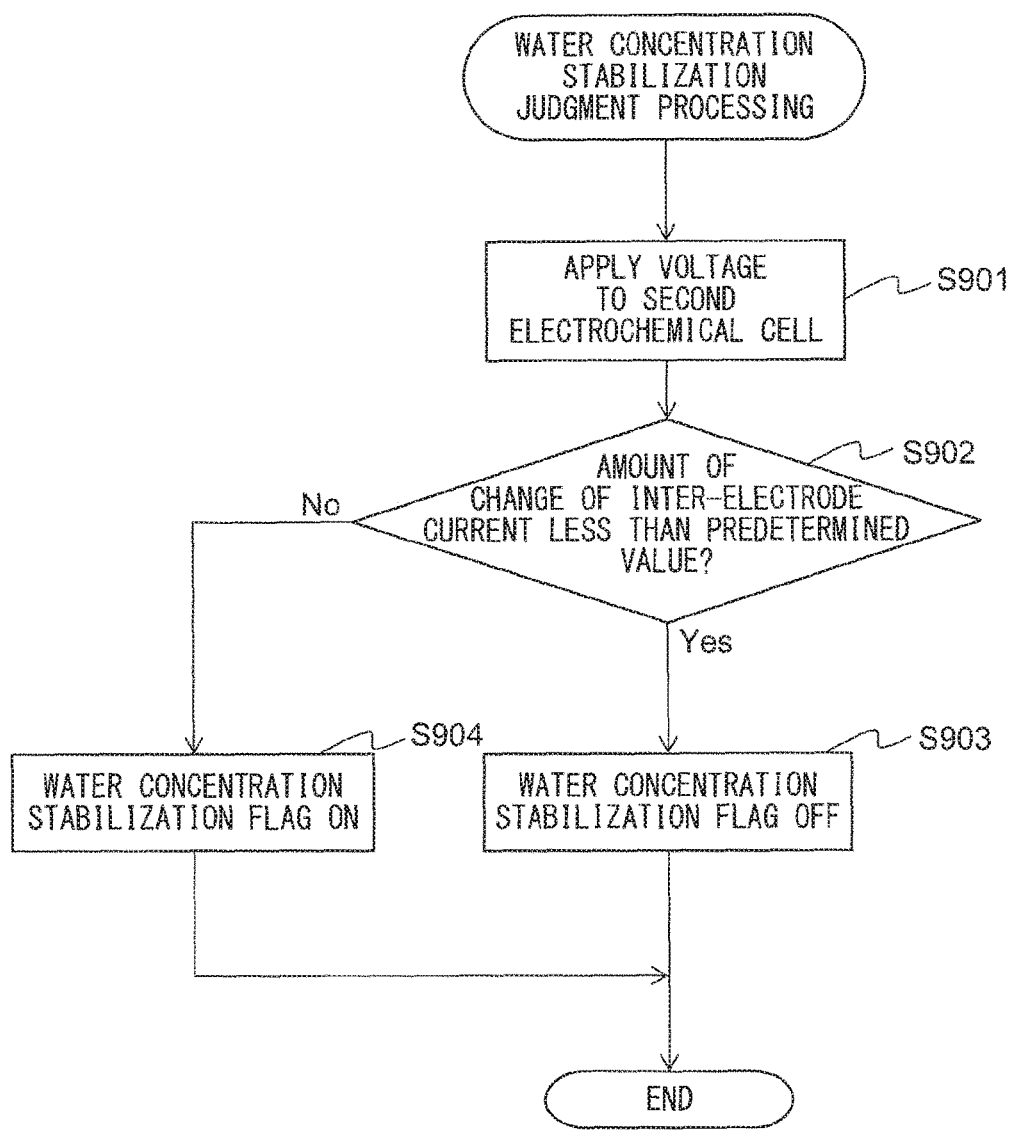

SULFUR OXIDES DETECTION SYSTEM

CROSS-REFERENCE TO RELATED APPLICATION

The present application claims priority to Japanese Patent Application No. 2015-229173 filed on Nov. 24, 2015, which is incorporated herein by reference in its entirety.

TECHNICAL FIELD

Embodiments of the present invention relates to a sulfur oxides detection system ($SO_X$ detection system) detecting a concentration of sulfur oxides ($SO_X$) in exhaust gas.

BACKGROUND ART

Fuel used in an internal combustion engine, in particular fossil fuel, contains trace amounts of sulfur (S) ingredients. The sulfur ingredients contained in fuel in this way invite deterioration of component parts in an exhaust system of an internal combustion engine etc. Further, if frequently performing control suppressing deterioration of the component parts due to the sulfur ingredients or control for regenerating deteriorated component parts, deterioration of the fuel efficiency is invited. Therefore, to keep the deterioration of the fuel efficiency etc. at a minimum extent while keeping the deterioration of the component parts at a minimum extent, it is desirable to detect the content of sulfur ingredients in the fuel.

If the fuel used in an internal combustion engine contains sulfur ingredients, the exhaust gas discharged from a combustion chamber contains sulfur oxides ($SO_X$). Further, the higher the content of the sulfur ingredients in the fuel, the higher the concentration of $SO_X$ in the exhaust gas. Therefore, if possible to detect the concentration of $SO_X$ in exhaust gas, it is possible to estimate the content of sulfur ingredients in the fuel.

Therefore, an exhaust gas sensor detecting the concentration of the $SO_X$ or other oxygen-containing gas components in the exhaust gas has been proposed (for example, see Japanese Patent Publication No. 11-190721A). This exhaust gas sensor has a measured gas chamber in which exhaust gas is introduced through a diffusion regulating layer, a first electrochemical cell, and a second electrochemical cell. In the first electrochemical cell, a relatively low voltage is applied across the electrodes forming the first electrochemical cell. As a result, due to the oxygen pumping action of the first electrochemical cell, the oxygen in the measured gas chamber is removed without the $SO_X$ in the measured gas chamber being decomposed. On the other hand, in the second electrochemical cell, a relatively high voltage is applied across the electrodes forming the second electrochemical cell. As a result, the $SO_X$ contained in the exhaust gas after removal of oxygen by the first electrochemical cell is decomposed. In addition, the oxide ions generated due to the decomposition of this $SO_X$ are discharged from the measured gas chamber due to the oxygen pumping action of the second electrochemical cell and the concentration of $SO_X$ in the exhaust gas is detected by detecting the decomposition current flowing along with the discharge of oxide ions.

SUMMARY

Technical Problem

However, the concentration of $SO_X$ in the exhaust gas is extremely low. For this reason, the decomposition current detected by the above-mentioned exhaust gas sensor is also extremely small. Therefore, it is difficult to accurately detect the decomposition current of $SO_X$ by such an exhaust gas sensor.

Therefore, an object of embodiments of the present invention is to provide a sulfur oxides detection system able to improve the precision of detection of the concentration of $SO_X$ in the exhaust gas.

Solution to Problem

In order to solve the above problem, in a first embodiment, there is provided a sulfur oxides detection system including a device part arranged in an exhaust passage of an internal combustion engine and comprising a first electrochemical cell having a first solid electrolyte layer having oxide ion conductivity, a first electrode arranged on one surface of the first solid electrolyte layer so as to be exposed to measured gas, and a second electrode arranged on the other surface of the first solid electrolyte layer so as to be exposed to the atmospheric air, and a diffusion regulating layer regulating diffusion of the measured gas. A power supply supplying voltage is provided across the first electrode and the second electrode, as well as a detector detecting a first current correlation parameter correlated with a current flowing between the first electrode and the second electrode. A control part is also provided for controlling the power supply and acquiring the first current correlation parameter from the detector, wherein the control part controls the power supply so that a first voltage which is a decomposition start voltage of water and sulfur oxides or more is applied across the first electrode and the second electrode and calculates a concentration of sulfur oxides in the measured gas based on the first current correlation parameter detected by the detector when the first voltage is applied across the first electrode and the second electrode and the control part does not calculate the concentration of sulfur oxides in the measured gas when the control part judges that a concentration of water in the measured gas is not stable.

In a second embodiment, the device part further comprises a second electrochemical cell having a second solid electrolyte layer having oxide ion conductivity, a third electrode arranged on one surface of the second solid electrolyte layer so as to be exposed to the measured gas, and a fourth electrode arranged on the other surface of the second solid electrolyte layer so as to be exposed to the atmospheric air. The power supply applies voltage across the third electrode and the fourth electrode and the detector detects a second current correlation parameter correlated with a current flowing between the third electrode and the fourth electrode, and the control part controls the power supply so that a second voltage which is a decomposition start voltage of water or more is applied across the third electrode and the fourth electrode and judges that the concentration of water in the measured gas is not stable if an amount of change of the second current correlation parameter detected by the detector is a predetermined value or more when the second voltage is applied across the third electrode and the fourth electrode, in the first embodiment.

In a third embodiment, the control part controls the power supply so that a third voltage which is a decomposition start voltage of water or more is applied across the first electrode and the second electrode and judges that the concentration of water in the measured gas is not stable if an amount of change of the first current correlation parameter detected by the detector is a predetermined value or more if the third voltage is applied across the first electrode and the second electrode, in the first or second embodiments.

In a forth embodiment, the sulfur oxides detection system further comprises a humidity sensor arranged in an intake passage of the internal combustion engine, and the control part judges that the concentration of water in the measured gas is not stable if an amount of change of humidity of the intake air detected by the humidity sensor is a predetermined value or more, in any one of the first to third embodiments.

In a fifth embodiment, the control part judges that the concentration of water in the measured gas is not stable if it judges that a fuel fed to a combustion chamber of the internal combustion engine is being switched, in any one of the first to fourth embodiments.

In a sixth embodiment, the system further comprises an ethanol concentration sensor arranged in a feed path of fuel fed to the combustion chamber, and the control part judges that the fuel is being switched if an amount of change of the concentration of ethanol in the fuel detected by the ethanol concentration sensor is a predetermined value or more, in the fifth embodiment.

In a seventh embodiment, the system further comprises an air-fuel ratio sensor arranged in the exhaust passage, and the control part controls a fuel amount fed to the combustion chamber by feedback so that the air-fuel ratio detected by the air-fuel ratio sensor becomes a target air-fuel ratio, and judges that the fuel is being switched if the target air-fuel ratio is maintained constant and an amount of change of the ratio between an amount of intake air fed to the combustion chamber and the fuel amount fed to the combustion chamber is a predetermined value or more, in the fifth embodiment.

In an eighth embodiment, the control part judges the fuel is being switched in the period from when a fuel tank of the internal combustion engine is filled with fuel to when a predetermined amount or more of fuel is fed to the combustion chamber, in the fifth embodiment.

In a ninth embodiment, the control part judges that the concentration of water in the measured gas is not stable if it determines that there is condensed water at least at one of an EGR passage connecting an intake passage of the internal combustion engine with the exhaust passage and the exhaust passage or that condensed water will be formed at least at one of the EGR passage and the exhaust passage, in any one of the first to eighth embodiments.

In a tenth embodiment, the control part judges that the concentration of water in the measured gas is not stable in the period from when water or an aqueous solution is injected into a path by which the measured gas reaches the device part to when the control part judges that the injected water or aqueous solution passes the device part in the exhaust passage, in any one of the first to ninth embodiments.

In an eleventh embodiment, the control part calculates the concentration of sulfur oxides in the measured gas if judging that an exhaust air-fuel ratio of exhaust gas discharged from a combustion chamber of the internal combustion engine is stable and that the concentration of water in the measured gas is stable, in any one of the first to tenth embodiments.

Advantageous Effects of Embodiments of the Present Invention

According to embodiments of the present invention, there is provided a sulfur oxides detection system able to improve the precision of detection of the concentration of $SO_X$ in the exhaust gas.

BRIEF DESCRIPTION OF DRAWINGS

FIG. 1 is a view schematically showing an internal combustion engine in which an $SO_X$ detection system according to a first embodiment of the present invention is used.

FIG. 14 is a flow chart showing a control routine of water concentration stability judgment processing in an eighth embodiment of the present invention.

DESCRIPTION OF EMBODIMENTS

Figure 2:
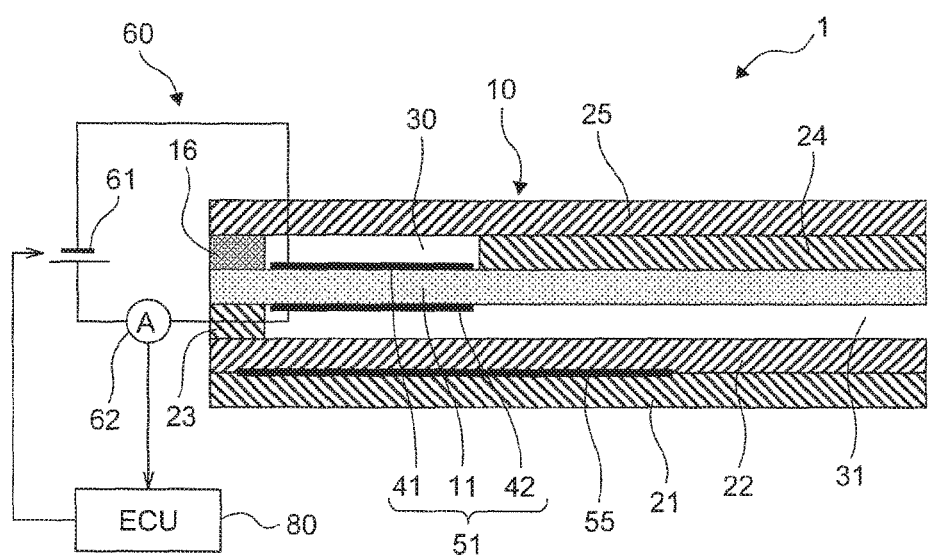
FIG. 2 is a schematic cross-sectional view showing the configuration of an $SO_X$ detection system according to the first embodiment of the present invention.

Below, referring to the drawings, embodiments of the present invention will be explained in detail. Note that, in the following description, similar component elements will be assigned the same reference notations.

<First Embodiment>

First, referring to FIG. 1 to FIG. 6, a first embodiment of the present invention will be explained.

<Explanation of Internal Combustion Engine as a Whole>

FIG. 1 is a view schematically showing an internal combustion engine in which a sulfur oxides detection system according to the first embodiment of the present invention (below, referred to as "$SO_X$ detection system") is used. The internal combustion engine shown in FIG. 1 is a compression self-ignition type internal combustion engine (diesel engine). The internal combustion engine is, for example, carried in a vehicle.

Referring to FIG. 1, the internal combustion engine comprises an engine body 100, a combustion chamber 2 of each cylinder, an electronic control type fuel injector 3 injecting fuel into each combustion chamber 2, an intake manifold 4, and an exhaust manifold 5. The intake manifold 4 is connected through an intake pipe 6 to an outlet of a compressor 7a of a turbocharger 7. An inlet of the compressor 7a is connected through the intake pipe 6 to an air cleaner 8. Inside the intake pipe 6, a throttle valve 9 driven by a step motor is arranged. Furthermore, around the intake pipe 6, a cooling device 14 is arranged for cooling the intake air flowing through the inside of the intake pipe 6. In the internal combustion engine shown in FIG. 1, engine cooling water is guided to the inside of the cooling device 13 where the engine cooling water is used to cool the intake air. The intake manifold 4 and intake pipe 6 form an intake passage guiding air to a combustion chamber 2.

On the other hand, the exhaust manifold 5 is connected through an exhaust pipe 27 to an inlet of a turbine 7b of the turbocharger 7. An outlet of the turbine 7b is connected through the exhaust pipe 27 to a casing 29 housing an exhaust purification catalyst 28. The exhaust manifold 5 and exhaust pipe 27 form an exhaust passage discharging exhaust gas formed due to combustion of the air-fuel mixture in the combustion chamber 2. The exhaust purification catalyst 28 is, for example, a selective reduction type $NO_X$ reduction catalyst removing $NO_X$ in exhaust gas by reduction (SCR catalyst) or an $NO_X$ storage reduction catalyst. Further, in the exhaust passage, to reduce the particulate matter (PM) in the exhaust gas, an oxidation catalyst, diesel particulate filter (DPF), etc. may be arranged.

The exhaust manifold 5 and the intake manifold 4 are connected with each other through an exhaust gas recirculation (below, "EGR") passage 14. Inside the EGR passage 14, an electronic control type EGR control valve 15 is arranged. Further, around the EGR passage 14, an EGR cooling device 20 is arranged for cooling the EGR gas flowing through the inside of the EGR passage 14. In the embodiment shown in FIG. 1, engine cooling water is guided to the inside of the cooling device 20 where the engine cooling water is used to cool the EGR gas.

The fuel is supplied by an electronic control type variable discharge fuel pump 19 from a fuel tank 33 through a fuel pipe 34 to the inside of a common rail 18. The fuel supplied to the inside of the common rail 18 is supplied through each fuel feed tube 17 to fuel injectors The various control routines of the internal combustion engine are performed by the electronic control unit (ECU) 80. The ECU 80 is a digital computer provided with components connected with each other by a bidirectional bus 81 such as a ROM (read only memory) 82, RAM (random access memory) 83, CPU (microprocessor) 84, input port 85, and output port 86. The outputs of a load sensor 101, air flow meter 102, humidity sensor 103, air-fuel ratio sensor 104, exhaust temperature sensor 105, ethanol concentration sensor 106, fuel level sensor 107, outside air temperature sensor 109, and water temperature sensor 110 are input through corresponding AD converters 87 to the input port 85. On the other hand, the output port 86 is connected through corresponding drive circuits 88 to the fuel injectors 3, throttle valve drive step motor, EGR control valve 15, and fuel pump 19.

The load sensor 101 generates an output voltage proportional to an amount of depression of an accelerator pedal 120. Therefore, the load sensor 101 detects an engine load. The air flow meter 102 is arranged in the intake passage between the air cleaner 8 and the compressor 7a and detects the air flow rate flowing through the inside of the intake pipe 6. The humidity sensor 103 is arranged in the intake passage between the air cleaner 8 and the compressor 7a and detects the humidity inside the intake pipe 6. Therefore, the humidity sensor 103 can detect the humidity of the intake air supplied to the combustion chambers 2. Note that the humidity sensor 103 may be integral with the air flow meter 102. Further, the humidity sensor 103 and air flow meter 102 may be arranged at other positions in the intake passage.

The air-fuel ratio sensor 104 is arranged in the exhaust passage between the turbine 7b and the exhaust purification catalyst 28 and detects the exhaust air-fuel ratio of the exhaust gas. The exhaust temperature sensor 105 is arranged in the exhaust passage between the turbine 7b and the exhaust purification catalyst 28 and detects the temperature of the exhaust gas. The ethanol concentration sensor 106 is arranged in the fuel pipe 34 and detects the concentration of ethanol in the fuel. The fuel level sensor 107 is arranged inside the fuel tank 33 and detects the amount of fuel inside the fuel tank 33. The outside air temperature sensor 109 is arranged at the vehicle at which the internal combustion engine is mounted and detects the outside air temperature of the internal combustion engine. The water temperature sensor 110 is arranged in the cooling water path of the internal combustion engine and detects the water temperature of the cooling water of the internal combustion engine. Furthermore, a crank angle sensor 108 generating an output pulse each time a crankshaft rotates by, for example, 15° is connected to the input port 85. The crank angle sensor 108 detects the engine speed.

<Explanation of $SO_X$ Detection System>

Below, referring to FIG. 1 and FIG. 2, an $SO_X$ detection system 1 according to the first embodiment of the present invention will be explained. The $SO_X$ detection system 1 detects the concentration of sulfur oxides ($SO_X$) in the exhaust gas flowing through the inside of the exhaust passage of the internal combustion engine.

FIG. 2 is a schematic cross-sectional view showing the configuration of an $SO_X$ detection system 1 according to the first embodiment of the present invention. As shown in FIG. 2, the $SO_X$ detection system 1 comprises a device part 10, a first circuit 60 connected to the device part 10, and the ECU 80. As shown in FIG. 1, the device part 10 is arranged in the exhaust passage of the internal combustion engine between the turbine 7b and the exhaust purification catalyst 28. In other words, the device part 10 is arranged in the exhaust passage at the upstream side of the exhaust purification catalyst 28 in the exhaust flow direction. Note that the device part 10 may be arranged at another position of the exhaust passage, for example, at the downstream side of the exhaust purification catalyst 28 in the exhaust flow direction.

As shown in FIG. 2, the device part 10 is configured by a plurality of layers stacked together. Specifically, the device part 10 comprises a first solid electrolyte layer 11, diffusion regulating layer 16, first barrier layer 21, second barrier layer 22, third barrier layer 23, fourth barrier layer 24, and fifth barrier layer 25.

The first solid electrolyte layer 11 is a thin sheet member having oxide ion conductivity. The first solid electrolyte layer 11 is, for example, formed by a sintered member of $ZrO_2$(zirconia), $HfO_2$, $ThO_2$, $Bi_2O_3$, to which CaO, MgO, $Y_2O_3$, $Yb_2O_3$, etc. is added as a stabilizer. Further, the diffusion regulating layer 16 is a thin sheet member having gas permeability. The diffusion regulating layer 16 is, for example, formed by a porous sintered body of alumina, magnesia, silica, spinel, mullite, or other heat resistant inorganic substance. The barrier layers 21 to 25 are thin sheet members having a gas barrier property and are formed, for example, as layers containing alumina.

The layers of the device part 10 are stacked, from the bottom of FIG. 2, in the order of the first barrier layer 21, second barrier layer 22, third barrier layer 23, first solid electrolyte layer 11, diffusion regulating layer 16 and fourth barrier layer 24, and fifth barrier layer 25. The first solid electrolyte layer 11, diffusion regulating layer 16, fourth barrier layer 24, and fifth barrier layer 25 are used to define and form a measured gas chamber 30. The measured gas chamber 30 is configured so that when the device part 10 is arranged in the exhaust passage, the exhaust gas of the internal combustion engine (measured gas) flows into the measured gas chamber 30 through the diffusion regulating layer 16. That is, the device part 10 is arranged in the exhaust passage so that the diffusion regulating layer 16 is exposed to the exhaust gas. Therefore, the measured gas chamber 30 communicates with the exhaust passage through the diffusion regulating layer 16. Note that the measured gas chamber 30 may be configured in any way so long as it adjoins the first solid electrolyte layer 11 and is configured so that the measured gas flows into it.

Further, the first solid electrolyte layer 11, second barrier layer 22, and third barrier layer 23 are used to define and form a first atmospheric chamber 31. As will be understood from FIG. 2, the first atmospheric chamber 31 is arranged across the first solid electrolyte layer 11 at the side opposite to the measured gas chamber 30. The first atmospheric chamber 31 is open to the atmospheric air outside the exhaust passage. Therefore, atmospheric air flows into the first atmospheric chamber 31. Note that the first atmospheric chamber 31 may be configured in any way so long as it adjoins the first solid electrolyte layer 11 and is configured so that atmospheric air flows into it.

The device part 10 is further provided with a first electrode 41 and a second electrode 42. The first electrode 41 is arranged on the surface of the first solid electrolyte layer 11 at the measured gas chamber 30 side. Therefore, the first electrode 41 is exposed to the measured gas in the measured gas chamber 30. On the other hand, the second electrode 42 is arranged on the surface of the first solid electrolyte layer 11 at the first atmospheric chamber 31 side. Therefore, the second electrode 42 is exposed to the gas inside the first atmospheric chamber 31 (atmospheric air). The first electrode 41 and the second electrode 42 are arranged facing each other across the first solid electrolyte layer 11. The first electrode 41, first solid electrolyte layer 11, and second electrode 42 form the first electrochemical cell 51.

In the present embodiment, the material forming the first electrode 41 includes platinum (Pt), rhodium (Rh), palladium (Pd), and other platinum group elements or alloys of the same as main ingredients. Preferably, the first electrode 41 is a porous cermet electrode containing at least one of platinum (Pt), rhodium (Rh), and palladium (Pd) as main ingredients. However, the material forming the first electrode 41 is not necessarily limited to the above materials. It may be any material so long as when a predetermined voltage is applied between the first electrode 41 and the second electrode 42, it can decompose by reduction the water and $SO_X$ contained in the measured gas inside the measured gas chamber 30.

Further, in the present embodiment, the second electrode 42 is a porous cermet electrode containing platinum (Pt) as a main ingredient. However, the material forming the second electrode 42 is not necessarily limited to the above material and may be any material which, when a predetermined voltage is applied between the first electrode 41 and the second electrode 42, can make oxide ions move between the first electrode 41 and the second electrode 42.

The device part 10 further comprises a heater (electric heater) 55. In the present embodiment, the heater 55, as shown in FIG. 2, is arranged between the first barrier layer 21 and the second barrier layer 22. The heater 55 is, for example, a thin sheet member of cermet containing platinum (Pt) and a ceramic (for example, alumina etc.) and is a heat generating member generating heat by application of current. The heater 55 can heat the first electrochemical cell 51 to an activation temperature or more. The output port 86 of the ECU 80 is connected through a corresponding drive circuit 88 to the heater 55. Therefore, the ECU 80 can control the heater 55 to control the temperature of the device part 10, in particular the first electrochemical cell 51.

As shown in FIG. 2, the first circuit 60 comprises a first power supply 61 and a first ammeter 62. The first power supply 61 applies voltage across the first electrode 41 and the second electrode 42 so that the potential of the second electrode 42 becomes higher than the potential of the first electrode 41. The output port 86 of the ECU 80 is connected through a corresponding drive circuit 88 to the first power supply 61. Therefore, the ECU 80 controls the first power supply 61 to control the voltage applied across the first electrode 41 and the second electrode 42.

The first ammeter 62 detects the current flowing between the first electrode 41 and the second electrode 42 (that is, the current flowing through the inside of the first solid electrolyte layer 11), that is, the inter-electrode current. The output of the first ammeter 62 is input through a corresponding AD converter 87 to the input port 85 of the ECU 80. Therefore, the ECU 80 can obtain the inter-electrode current detected by the first ammeter 62 from the first ammeter 62.

<Principle of Detection of $SO_X$ Concentration>

Next, the principle of detection of $SO_X$ by the $SO_X$ detection system 1 will be explained. In explaining the principle of detection of $SO_X$, first, the limit current characteristic of oxygen in the device part 10 will be explained. At the device part 10, if applying voltage across the electrodes using the first electrode 41 at the measured gas chamber 30 side as the cathode and the second electrode 42 at the first atmospheric chamber 31 side as the anode, the oxygen contained in the measured gas is decomposed by reduction and becomes oxide ions. The oxide ions are conducted through the first solid electrolyte layer 11 of the first electrochemical cell 51 from the cathode side to the anode side where they become oxygen which is discharged into the atmosphere. In this Description, such a movement of oxygen by conduction of oxide ions from the cathode side to anode side through the solid electrolyte layer will be called the "oxygen pumping action".

Due to the conduction of oxide ions accompanying such an oxygen pumping action, an inter-electrode current flows across the first electrode 41 and the second electrode 42 forming the first electrochemical cell 51. This inter-electrode current becomes larger the higher the voltage applied between the first electrode 41 and the second electrode 42. This is because the higher the applied voltage, the greater the amount of conduction of oxide ions.

However, if the applied voltage is gradually raised and becomes a certain fixed value or more, the inter-electrode current can no longer become larger and is held at a constant value. Such a characteristic is called the "limit current characteristic of oxygen", while the voltage region where the limit current characteristic of oxygen occurs is called the "limit current region of oxygen". Such a limit current characteristic of oxygen occurs due to the speed of conduction of oxide ions able to be conducted through the inside of the solid electrolyte layers 11, 12 along with application of voltage exceeding the speed of introduction of oxygen introduced into the measured gas chamber 30 through the diffusion regulating layer 16. That is, it occurs due to the decomposition reaction of oxygen by reduction at the cathode being a state regulated in diffusion.

Therefore, the inter-electrode current (limit current) when a voltage in the limit current region is applied to the first electrochemical cell 51 corresponds to the concentration of oxygen in the measured gas. By utilizing such a limit current characteristic of oxygen, it is possible to detect the concentration of oxygen in the measured gas and use the detected concentration as the basis to detect the air-fuel ratio of the exhaust gas.

In this regard, the above-mentioned oxygen pumping action is not an action expressed only in the oxygen contained in the measured gas. In gases containing oxygen atoms in the molecules, there are also gases where the oxygen pumping action can be expressed. As such a gas, $SO_X$ and water ($H_2O$) may be mentioned. Therefore, by applying a voltage of the decomposition start voltage of the $SO_X$ and water or more between the first electrode 41 and the second electrode 42 of the first electrochemical cell 51, the water and $SO_X$ contained in the measured gas are decomposed. The oxide ions generated due to the decomposition of $SO_X$ and water are conducted by the oxygen pumping action from the first electrode 41 to the second electrode 42. For this reason, inter-electrode current flows between the first electrode 41 and the second electrode 42.

However, the concentration of $SO_X$ in the exhaust gas is extremely low. The inter-electrode current which is generated due to decomposition of $SO_X$ is also extremely small. In particular, exhaust gas contains a large amount of water and due to the decomposition of water, inter-electrode current flows. For this reason, it is difficult to precisely detect the inter-electrode current occurring due to decomposition of $SO_X$ separately.

As opposed to this, the inventors of the present application discovered that in an electrochemical cell having an oxygen pumping action, the decomposition current when the water and $SO_X$ are decomposed changes depending on the concentration of $SO_X$ in the exhaust gas. The specific principle why this phenomenon occurs is not necessarily clear, but it is believed that this occurs due to the following mechanism.

As explained above, if applying a predetermined voltage of the decomposition start voltage of $SO_X$ or more across the first electrode 41 and the second electrode 42 of the first electrochemical cell 51, the $SO_X$ contained in the measured gas is decomposed. As a result, the decomposition products of the $SO_X$ (for example, sulfur and sulfur compounds) are adsorbed on the cathode comprised of the first electrode 41. As a result, the area of the first electrode able to contribute to the decomposition of water decreases. If the concentration of $SO_X$ in the measured gas is high, decomposition products adsorbed on the first electrode 41 become more. As a result, the decomposition current of water flowing between the electrodes when applying a predetermined voltage of the decomposition start voltage of water or more across the first electrode 41 and the second electrode 42 becomes relatively small. On the other hand, if the concentration of $SO_X$ in the measured gas is low, decomposition products adsorbed on the first electrode 41 becomes less. As a result, the decomposition current of water flowing between the electrodes when applying a predetermined voltage of the decomposition start voltage of water or more across the first electrode 41 and the second electrode 42 becomes relatively high. Therefore, the decomposition current of water flowing between the electrodes changes in accordance with the concentration of $SO_X$ in the measured gas. Using this phenomenon, it becomes possible to detect the concentration of $SO_X$ in the measured gas.

Here, the decomposition start voltage of water is seen to fluctuate somewhat depending on the measurement conditions etc., but is about 0.6V. Further, the decomposition start voltage of $SO_X$ is the same extent as the decomposition start voltage of water or slightly lower than that. Therefore, in the present embodiment, to use the above method to detect the concentration of $SO_X$ in the measured gas by the first electrochemical cell 51, 0.6V or more of voltage is applied across the first electrode 41 and the second electrode 42. Further, if the applied voltage is too high, breakdown of the first solid electrolyte layer 11 may be invited. In this case, it is difficult to precisely detect the concentration of $SO_X$ in the measured gas based on the inter-electrode current. For this reason, in the present embodiment, to use the above method to detect the concentration of $SO_X$ in the measured gas, a voltage of 0.6V to less than 2.0V is applied across the first electrode 41 and the second electrode 42.

Figure 3:
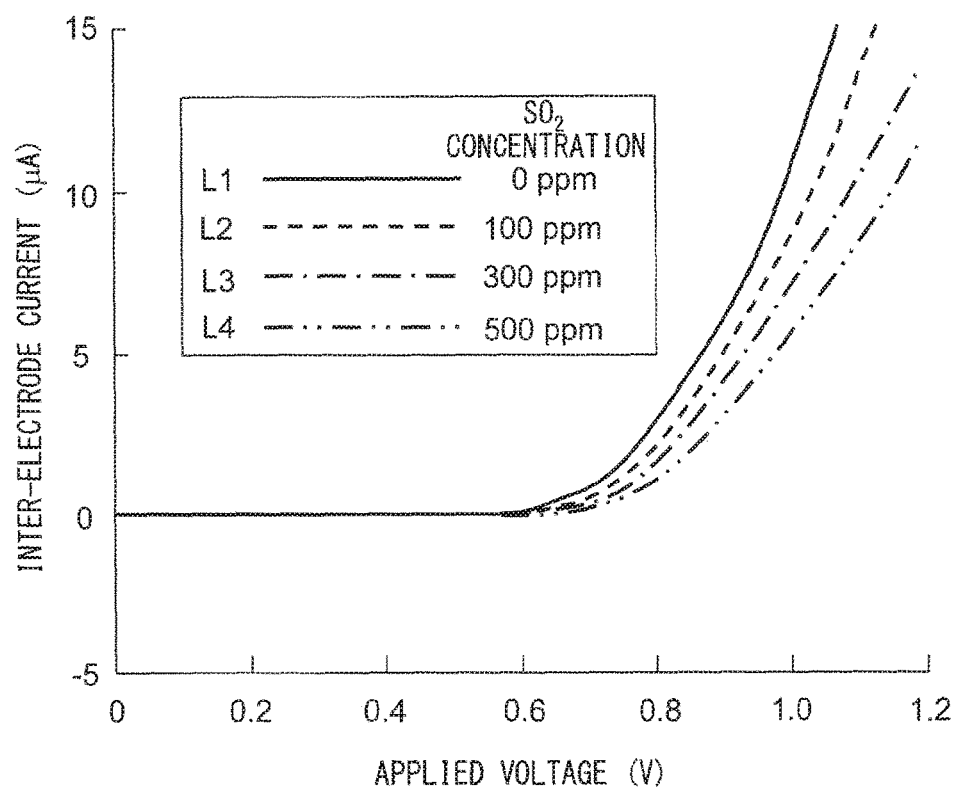
FIG. 3 is a view showing the relationship between the voltage applied across electrodes of a first electrochemical cell and an inter-electrode current flowing across electrodes of the first electrochemical cell.

Below, the relationship between the applied voltage and the inter-electrode current will be specifically explained. FIG. 3 is a schematic graph showing the relationship between the applied voltage and inter-electrode current when gradually raising the applied voltage (pressure raising sweep) in the first electrochemical cell 51. In the illustrated example, four types of measured gas with different concentrations of the $SO_2$ (that is, $SO_N$) contained in the measured gas (0 ppm, 100 ppm, 300 ppm, and 500 ppm) were used. Note that the concentration of oxygen in the measured gas reaching the first electrode (cathode) 41 of the first electrochemical cell 51 is maintained constant (about 0 ppm) no matter what the measured gas.

The solid line L1 in FIG. 3 shows the relationship between the applied voltage and the inter-electrode current when the $SO_2$ concentration in the measured gas is 0 ppm. In the example shown in FIG. 3, the concentration of oxygen in the measured gas is maintained at substantially 0 ppm, so in the region where the applied voltage is less than about 0.6V, the inter-electrode current is substantially 0. On the other hand, if the applied voltage becomes about 0.6V or more, the inter-electrode current starts to increase along with an increase of the applied voltage. The increase of this inter-electrode current is due to the start of decomposition of water at the first electrode 41.

The broken line L2 in FIG. 3 shows the relationship between the applied voltage and the inter-electrode current in the case where the $SO_2$ concentration in the measured gas is 100 ppm. In this case as well, in the region where the applied voltage is less than about 0.6V, in the same way as the case of the solid line L1, the inter-electrode current is substantially 0. On the other hand, when the applied voltage is about 0.6V or more, inter-electrode current flows due to decomposition of water. However, the inter-electrode current at this time (broken line L2) is smaller compared with the solid line L1. Further, the rate of increase of the inter-electrode current with respect to the applied voltage (slope of broken line L2) also is smaller compared with the solid line L1.

The one-dot chain line L3 in FIG. 3 shows the relationship between the applied voltage and the inter-electrode current in the case where the $SO_2$ concentration in the measured gas is 300 ppm. Further, the two-dot chain line L4 in FIG. 3 shows the relationship between the applied voltage and the inter-electrode current when the $SO_2$ concentration in the measured gas is 500 ppm. In these cases as well, in the region where the applied voltage is less than about 0.6V, in the same way as the case of the solid line L1 and broken line L2, the inter-electrode current becomes substantially 0. On the other hand, when the applied voltage is about 0.6V or more, inter-electrode current flows due to the decomposition of water. However, the higher the concentration of $SO_2$ in the measured gas, the smaller the inter-electrode current and the smaller the rate of increase of the inter-electrode current with respect to the applied voltage (slopes of one-dot chain line L3 and two-dot chain line L4).

In this way, from the example shown in FIG. 3 as well, it will be understood that the magnitude of the inter-electrode current when the applied voltage is the decomposition start voltage of $SO_X$ and water of about 0.6V or more changes according to the concentration of $SO_2$ (that is, $SO_X$) contained in the measured gas. For example, if plotting the magnitude of the inter-electrode current at the lines L1 to L4 when the applied voltage in the graph shown in FIG. 3 is 1.0V with respect to the concentration of $SO_2$ in the measured gas, the graph shown in FIG. 4 is obtained.

Figure 4:
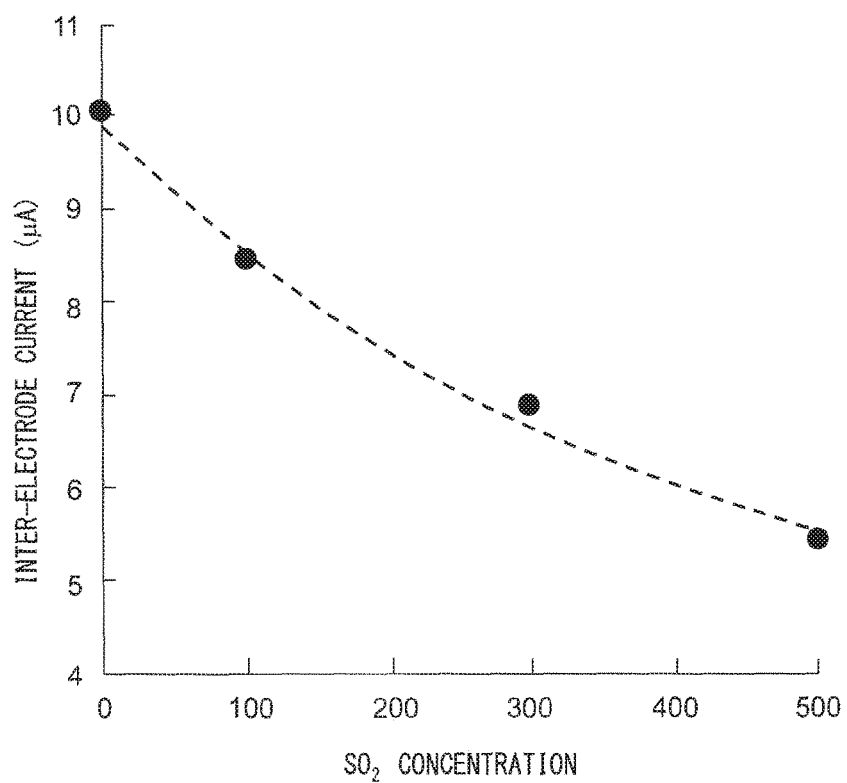
FIG. 4 is a view showing the relationship between a magnitude of the inter-electrode current when the applied voltage is 1.0V and a concentration of sulfur oxides in the measured gas.

As will be understood from FIG. 4, the magnitude of the inter-electrode current in the case of applying a predetermined voltage (in the example shown in FIG. 4, 1.0V) changes depending on the concentration of $SO_2$ (that is, $SO_X$) contained in the measured gas. Therefore, as explained above, it is possible to detect the $SO_X$ concentration based on the inter-electrode current when applying a predetermined voltage of the decomposition start voltage of water and $SO_X$ or more.

<Control for Detecting $SO_X$ Concentration>

Therefore, in the present embodiment, the concentration of $SO_X$ in the measured gas is detected in the following way. In the present embodiment, to detect the concentration of $SO_X$ in the measured gas, the ECU 80 controls the first power supply 61 to apply a voltage of the decomposition start voltage of $SO_X$ and water or more over a predetermined time period to the first electrochemical cell 51. As a result, on the first electrode 41, decomposition products resulting from the decomposition of $SO_X$ are adsorbed. The voltage applied to the first electrochemical cell 51 is for example 1.1V. The ECU 80 acquires the inter-electrode current detected by the first ammeter 62 after the elapse of the above predetermined time period. This inter-electrode current changes according to the amount of adsorption of the decomposition products of $SO_X$ on the first electrode 41. Therefore, the ECU 80 can detect the concentration of $SO_X$ in the measured gas based on the inter-electrode current detected by the first ammeter 62 when voltage of the decomposition start voltage of $SO_X$ and water is applied to the first electrochemical cell 51.

However, the concentration of $SO_X$ in the exhaust gas changes due to not only the content of sulfur ingredients in the fuel but also the exhaust air-fuel ratio of the exhaust gas. In particular, if the exhaust air-fuel ratio is an air-fuel ratio leaner than the stoichiometric air-fuel ratio, the higher the lean degree of the exhaust air-fuel ratio (the larger the air-fuel ratio), the ratio of fuel to the air becomes lower. As a result, even if the content of the sulfur ingredients in the fuel is constant, the higher the lean degree of the exhaust air-fuel ratio, the lower the concentration of $SO_X$ in the exhaust gas. Therefore, if the exhaust air-fuel ratio is not stable, the precision of detection of the concentration of $SO_X$ in the measured gas falls.

Therefore, in the present embodiment, the ECU 80 judges if the exhaust air-fuel ratio is stable and, when it judges that the exhaust air-fuel ratio is not stable, does not calculate the concentration of $SO_X$ in the measured gas. Due to this, in the present embodiment, the precision of detection of the concentration of $SO_X$ in the exhaust gas can be improved.

Further, even when applying voltage of the decomposition start voltage of $SO_X$ and water or more across the electrodes for detecting the concentration of $SO_X$ in the measured gas, if the concentration of water in the measured gas is not stable, the inter-electrode current fluctuates. Specifically, if the concentration of water in the measured gas becomes higher, the amount of water decomposed on the first electrode 41 increases, so the inter-electrode current becomes larger. On the other hand, if the concentration of water in the measured gas becomes lower, the amount of water decomposed on the first electrode 41 is decreased, so the inter-electrode current becomes smaller. Therefore, if the concentration of water in the measured gas is not stable, the inter-electrode current fluctuates and the precision of detection of the concentration of $SO_X$ in the measured gas falls.

Therefore, in the present embodiment, the ECU 80 judges if the concentration of water in the measured gas is stable and if judging that the concentration of water in the measured gas is not stable, does not calculate the concentration of $SO_X$ in the measured gas. Due to this, in the present embodiment, it is possible to improve the precision of detection of the concentration of $SO_X$ in the measured gas. Note that "not calculating the $SO_X$ concentration" means not applying voltage to the first electrochemical cell 51, lowering the voltage applied to the first electrochemical cell 51 to less than the decomposition start voltage of $SO_X$ and water, applying voltage of the decomposition start voltage of $SO_X$ and water or more to the first electrochemical cell 51, but not acquiring inter-electrode current, and applying voltage of the decomposition start voltage of $SO_X$ and water or more to the first electrochemical cell 51 and acquiring the inter-electrode current, but not calculating the $SO_X$ concentration based on the inter-electrode current. Further, if the predetermined control of the internal combustion engine performed using the calculated $SO_X$ concentration is stopped, it can be said that the $SO_X$ concentration has not substantially been calculated.

In this regard, if the humidity of the intake air supplied to the combustion chamber 2 changes, the concentration of water in the measured gas also changes. For this reason, in the present embodiment, the ECU 80 judges that the concentration of water in the measured gas is not stable if the amount of change of the humidity of the intake air is a predetermined value or more.

<Control Routine of $SO_X$ Concentration Calculation Processing>

Figure 5:
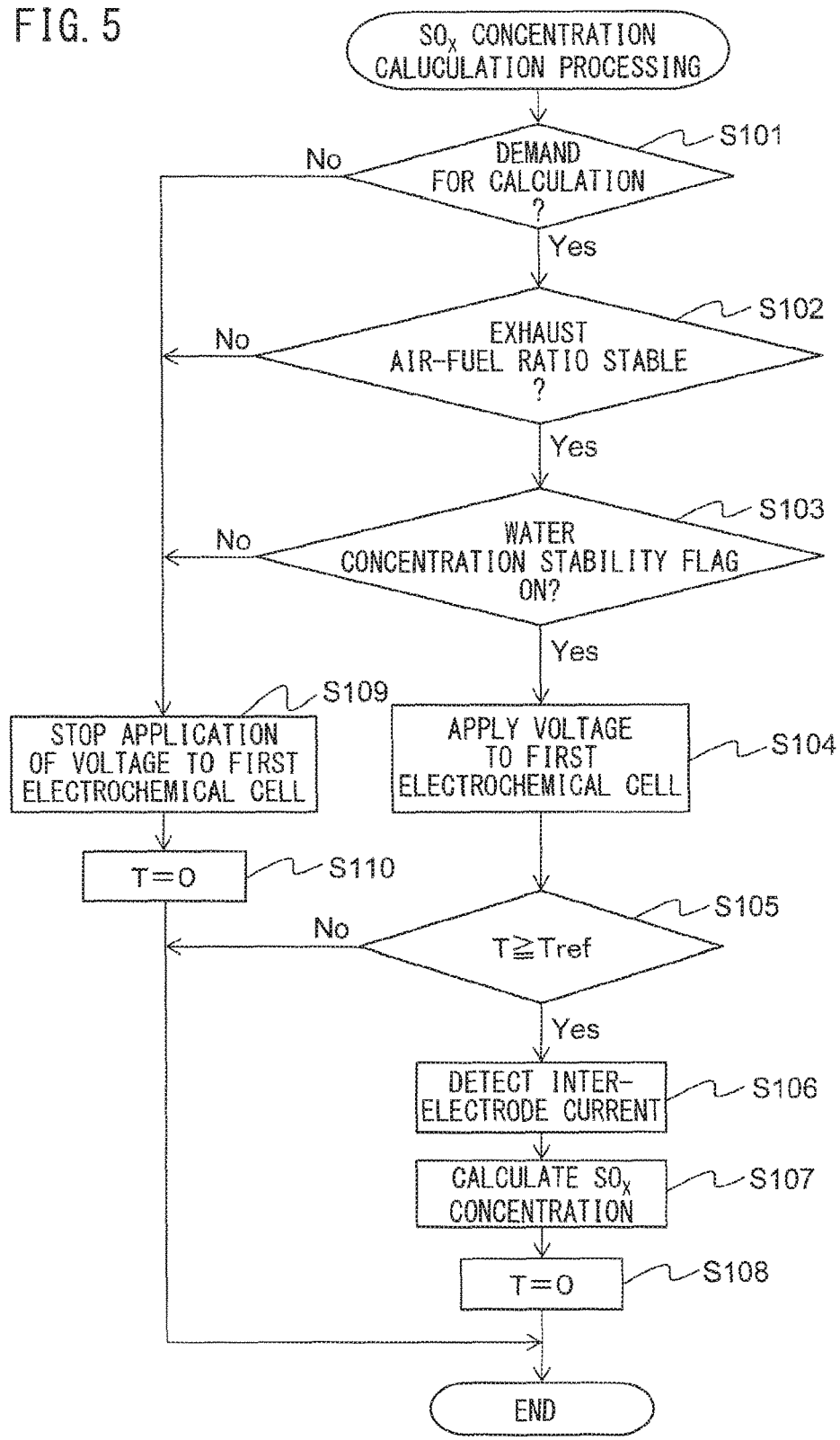
FIG. 5 is a flow chart showing a control routine of $SO_X$ concentration calculation processing in a first embodiment of the present invention.

FIG. 5 is a flow chart of the control routine of $SO_X$ concentration calculation processing in the first embodiment of the present invention. The illustrated control routine is repeatedly performed by the ECU 80 at predetermined time intervals.

First, at step S101, it is judged if there is a demand for calculation of the concentration of $SO_X$ in the measured gas. The demand for calculation of the $SO_X$ concentration is generated when, for example, the fuel tank 33 has been filled with fuel and is cancelled when the $SO_X$ concentration is calculated once or a plurality of times. Further, a demand for calculation of the $SO_X$ concentration may be generated when the ignition key is turned on and may be cancelled when the $SO_X$ concentration is calculated once or a plurality of times. If at step S101 it is judged that there is a demand for calculation of the concentration of $SO_X$ in the measured gas, the present control routine proceeds to step S102.

At step S102, it is judged if the exhaust air-fuel ratio of the exhaust gas discharged from the combustion chamber 2 is stable. As a specific example, it is judged if the amount of change of the exhaust air-fuel ratio is a predetermined value or less. The amount of change of the exhaust air-fuel ratio is calculated by for example the difference between a maximum value and a minimum value of the exhaust air-fuel ratio at a predetermined time. The exhaust air-fuel ratio is for example detected by the air-fuel ratio sensor 104. Note that the exhaust air-fuel ratio may be calculated from the ratio of the amount of intake air fed to the combustion chamber 2 and the amount of fuel fed to the combustion chamber 2. When it is judged at step S102 that the exhaust air-fuel ratio is stable, the present control routine proceeds to step S103.

At step S103, it is judged if the water concentration stability flag is on. The water concentration stability flag is a flag set by the later explained water concentration stability judgment processing. The water concentration stability flag is set on when it is judged that the concentration of water in the measured gas is stable and is set off when it is judged that the concentration of water in the measured gas is not stable. Further, the water concentration stability flag is set off even when the ignition key is turned to off. If at step S103 it is judged that the water concentration stability flag is on, the present control routine proceeds to step S104.

From step S104 to step S10, control is performed to calculate the concentration of $SO_X$ in the measured gas by the $SO_X$ detection system 1. Specifically, at step S104, voltage of the decomposition start voltage of the $SO_X$ and water or more is applied across the first electrode 41 and the second electrode 42 of the first electrochemical cell 51. The applied voltage is set to a voltage of 0.6V to less than 2.0V, for example, 1.1V.

Next, at step S105, it is judged if the elapsed time T from when starting to apply voltage to the first electrochemical cell 51 at step S104 is a reference time period Tref or more. The reference time period Tref is determined in advance by experiments or calculations. This is made a sufficient time for the decomposition products of $SO_X$ to be adsorbed on the first electrode 41 by application of voltage. If at step S105 it is judged that the elapsed time T is the reference time period Tref or more, the present control routine proceeds to step S106. On the other hand, if at step S105 it is judged that the elapsed time T is less than the reference time period Tref, the present control routine is ended.

At step S106, the inter-electrode current flowing between the first electrode 41 and the second electrode 42 is detected. Next, at step S107, the map such as shown in FIG. 4 is used to detect the concentration of $SO_X$ in the measured gas based on the inter-electrode current detected at step S106. In this map, it is shown that the concentration of $SO_X$ in the measured gas becomes higher the smaller the inter-electrode current. After step S107, the elapsed time T is reset and made zero at step S108. After this, the present control routine is ended.

On the other hand, if at step S101 it is judged that there is no demand for calculation of the concentration of $SO_X$ in the measured gas, when at step S102 it is judged that the exhaust air-fuel ratio is not stable or when at step S103 it is judged that the water concentration stability flag is off, the present control routine proceeds to step S109. At step S109, the application of voltage to the first electrochemical cell 51 is stopped. That is, the voltage applied to the first electrochemical cell 51 is made zero. Next, at step S110, the elapsed time T is reset and made zero. After this, the present control routine is ended.

Therefore, in the present control routine, if it is judged that the exhaust air-fuel ratio is not stable or if it is judged that the concentration of water in the measured gas is not stable, the concentration of $SO_X$ in the measured gas is not calculated. On the other hand, in the present control routine, if it is judged that the exhaust air-fuel ratio is stable and it is judged that the concentration of water in the measured gas is stable, the concentration of $SO_X$ in the measured gas is calculated.

Note that at step S109, instead of stopping the application of voltage to the first electrochemical cell 51, it is also possible to lower the voltage applied to the first electrochemical cell 51 to less than the decomposition start voltages of $SO_X$ and water. In this case, the applied voltage is for example set to 0.3V. Further, at step S106, as the current correlation parameter correlated with the inter-electrode current, a parameter other than the current value such as the resistance value may be detected. The current correlation parameter is detected by any detector which the $SO_X$ detection system 1 is provided with and is acquired by the ECU 80.

Further, in the present control routine, step S102 and step S103 are separate, but the judgments at step S102 and step S103 may be performed at the same step.

<Control Routine of Water Concentration Stability Judgment Processing>

Figure 6:
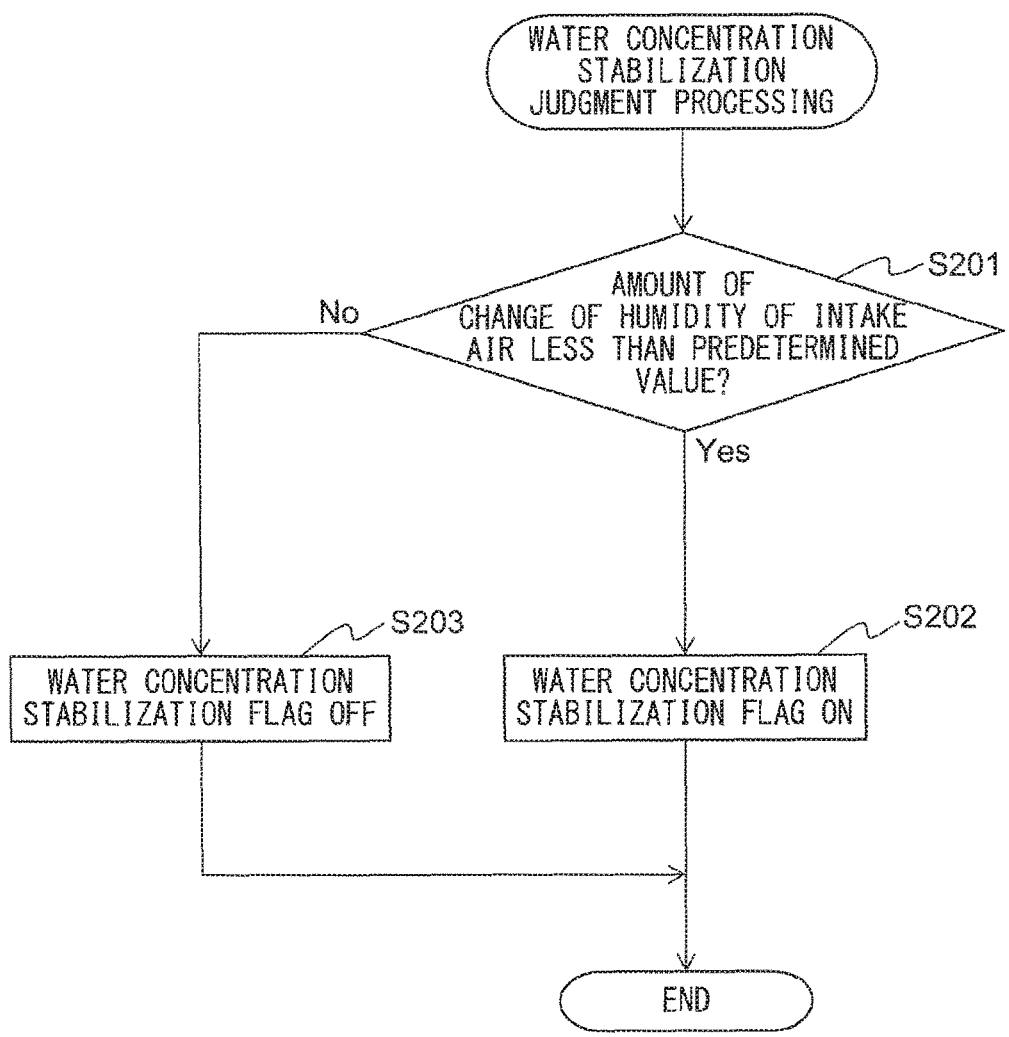
FIG. 6 is a flow chart showing a control routine of water concentration stability judgment processing in a first embodiment of the present invention.

FIG. 6 is a flow chart showing a control routine of water concentration stability judgment processing in a first embodiment of the present invention. The illustrated control routine is repeatedly performed by the ECU 80 at predetermined time intervals.

First, at step S201, it is judged if the amount of change of the humidity of the intake air fed to the combustion chamber 2 is less than a predetermined value. The amount of change of the humidity of the intake air is calculated, for example, by the difference between a maximum value and a minimum value of the humidity over a predetermined time. The humidity of the intake air is detected by the humidity sensor 103. Further, the above predetermined value at step S201 is determined in advance by experiments or calculations and is made a value corresponding to the lower limit value of the amount of change of the water concentration for which obtaining the desired precision of calculation of the $SO_X$ concentration is difficult. When at step S201 it is judged that the amount of change of the humidity of the intake air is less than a predetermined value, the present control routine proceeds to step S202.

In this case, it is considered that it is possible to obtain the desired precision of detection of the $SO_X$ concentration, so at step S202, the water concentration stability flag is set on. After this, the present control routine is ended. Therefore, in the present control routine, when the amount of change of the humidity of the intake air is less than a predetermined value, it is judged that the concentration of water in the measured gas is stable.

On the other hand, if at step S201 it is judged that the amount of change of the humidity of the intake air is a predetermined value or more, the present control routine proceeds to step S203. In this case, it is considered that it is not possible to obtain the desired precision of detection of the $SO_X$ concentration, so at step S203, the water concentration stability flag is set off. After this, the present control routine is ended. Therefore, in the present control routine, when the amount of change of the humidity of the intake air is a predetermined value or more, it is judged that the concentration of water in the measured gas is not stable.

<Second Embodiment>

Below, a second embodiment of the present invention will be explained focusing on the parts different from the first embodiment. In the second embodiment, in the same way as the first embodiment, the $SO_X$ detection system 1 shown in FIG. 2 is used to detect the concentration of $SO_X$ in the measured gas.

If filling the fuel tank 33 with fuel, sometimes a different type of fuel from the fuel in the fuel tank 33 is filled. It is known that the ratio of hydrogen with respect to the carbon in the fuel and the ratio of the oxygen with respect to the carbon in the fuel become higher the higher the concentration of ethanol in the fuel. For this reason, the concentration of water in the exhaust gas when burning an air-fuel mixture of the stoichiometric air-fuel ratio becomes higher the higher the ethanol concentration. Therefore, if the fuel in the fuel tank 33 is switched between fuels of different ethanol concentrations, the concentration of ethanol in the fuel changes and in turn the concentration of water in the exhaust gas changes. Therefore, in the second embodiment, if the ECU 80 judges that the fuel fed to the combustion chamber 2 is being switched, it judges that the concentration of water in the measured gas is not stable. Further, in the second embodiment, the ECU 80 judges that the fuel is being switched if the amount of change of the concentration of ethanol in the fuel is a predetermined value or more.

<Control Routine of Water Concentration Stability Judgment Processing>

Figure 7:
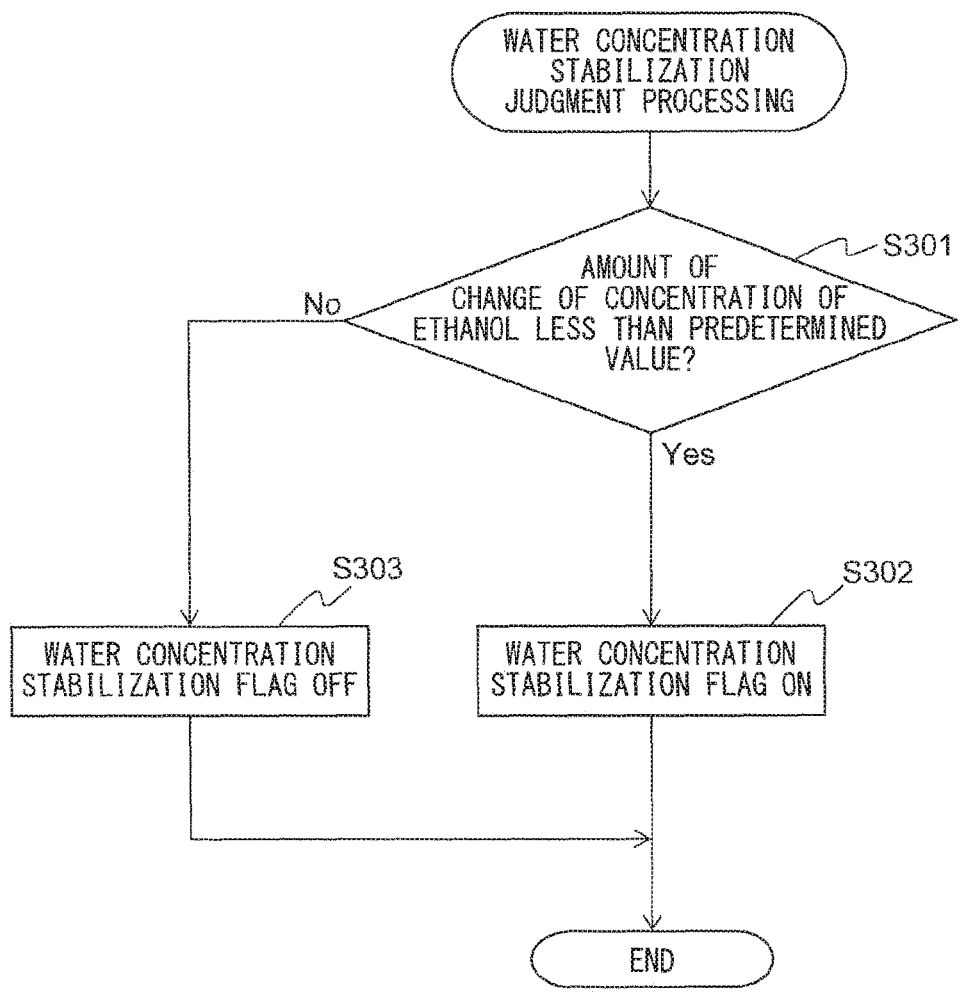
FIG. 7 is a flow chart showing a control routine of water concentration stability judgment processing in a second embodiment of the present invention.

In the second embodiment of the present invention, as the control routine of water concentration stability judgment processing, the control routine shown in FIG. 7 is executed. FIG. 7 is a flow chart showing a control routine of water concentration stability judgment processing in a second embodiment of the present invention. The illustrated control routine is repeatedly performed by the ECU 80 at predetermined time intervals.

First, at step S301 it is judged if the amount of change of the concentration of ethanol in the fuel fed to the combustion chamber 2 is less than a predetermined value. The amount of change of the concentration of ethanol in the fuel is for example calculated by the difference between a maximum value and a minimum value of the concentration of ethanol in the fuel at a predetermined time. The concentration of ethanol in the fuel is detected by the ethanol concentration sensor 106. Further, the above predetermined value at step S301 is determined in advance by experiments or calculations and is made the lower limit value of the amount of change of the ethanol concentration where it is estimated that the fuel is being switched. When at step S301 it is judged that the amount of change of the ethanol concentration is less than a predetermined value, the present control routine proceeds to step S302.

In this case, it is considered that it is possible to obtain the desired precision of calculation of the $SO_X$ concentration, so, at step S302, the water concentration stability flag is set on. After this, the present control routine is ended. Therefore, in the present control routine, when the amount of change of the ethanol concentration is less than a predetermined value, it is judged that the concentration of water in the measured gas is stable.

On the other hand, when at step S301 it is judged that the amount of change of the ethanol concentration is a predetermined value or more, that is, when it is judged that the fuel is being switched, at step S303, the water concentration stability flag is set off. After step S303, the present control routine is ended. Therefore, in the present control routine, if the amount of change of the ethanol concentration is a predetermined value or more, it is judged that the concentration of water in the measured gas is not stable.

Note that the ethanol concentration sensor 106 may be arranged at a position other than the fuel pipe 34, for example, in the fuel tank 33 so long as in the feed path of the fuel fed to the combustion chamber 2.

<Third Embodiment>

Below, a third embodiment of the present invention will be explained focusing on the parts different from the first embodiment and the second embodiment. In the third embodiment, in the same way as the first embodiment, the $SO_X$ detection system 1 shown in FIG. 2 is used to detect the concentration of $SO_X$ in the measured gas. Further, in the third embodiment, the ECU 80 uses a method different from the second embodiment to judge if the fuel is being switched.

In the third embodiment, the ECU 80 controls the amount of fuel fed to the combustion chamber 2 by feedback so that the air-fuel ratio detected by the air-fuel ratio sensor 104 becomes a target air-fuel ratio. In this case, if the target air-fuel ratio is maintained constant (for example, stoichiometric air-fuel ratio), the ratio of the amount of intake air fed to the combustion chamber 2 and the amount of fuel fed to the combustion chamber 2 becomes substantially constant. However, the value of the stoichiometric air-fuel ratio changes in accordance with the concentration of ethanol in the fuel. For this reason, if fuel is switched between fuels of different ethanol concentrations, even if the target air-fuel ratio is maintained constant (for example, stoichiometric air-fuel ratio), the ratio of the amount of intake air and the amount of fuel changes due to the above feedback control. Therefore, in the third embodiment, the ECU 80 judges that the fuel is being switched if the target air-fuel ratio is maintained constant and the amount of change of the ratio of the amount of intake air and the amount of fuel is a predetermined value or more. Further, the ECU 80 judges that the concentration of water in the measured gas is not stable if judging that the fuel is being switched.

<Control Routine of Water Concentration Stability Judgment Processing>

Figure 8:
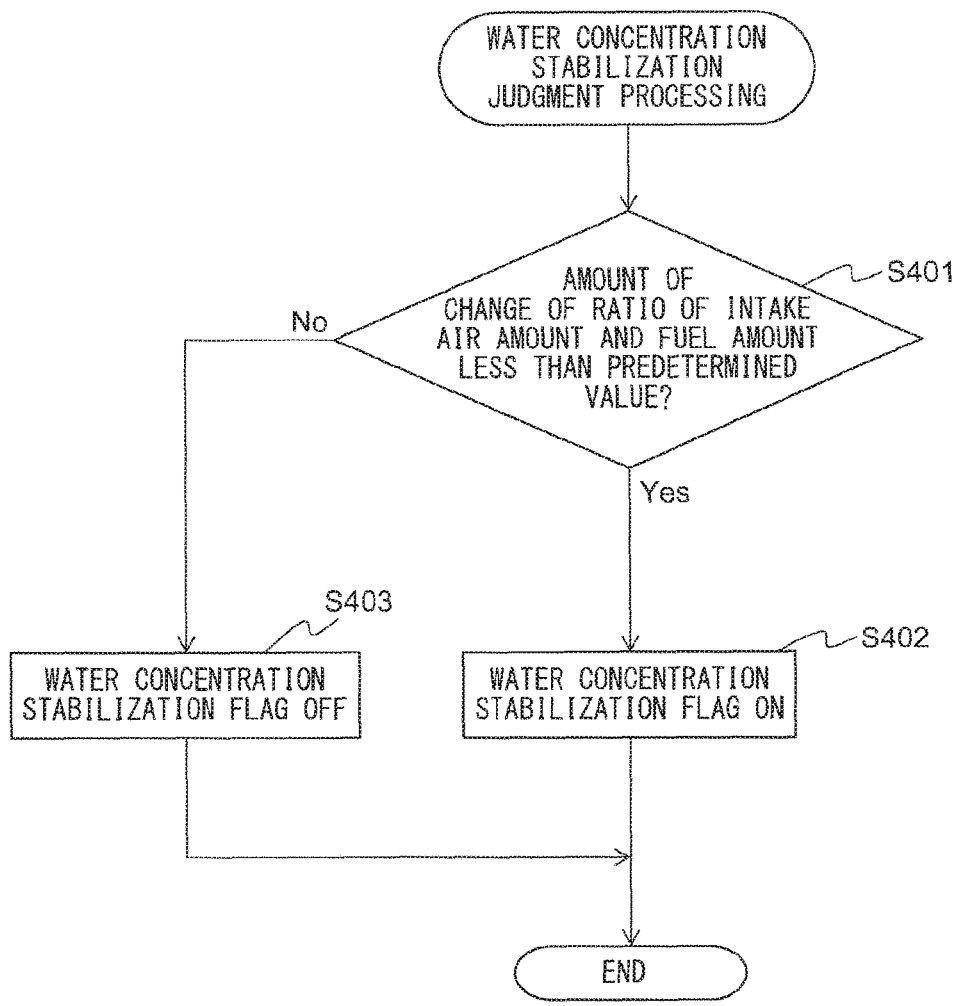
FIG. 8 is a flow chart showing a control routine of water concentration stability judgment processing in a third embodiment of the present invention.

In the third embodiment, as the control routine of water concentration stability judgment processing, the control routine shown in FIG. 8 is performed. FIG. 8 is a flow chart showing a control routine of water concentration stability judgment processing in a third embodiment of the present invention. The illustrated control routine is repeatedly performed by the ECU 80 at predetermined time intervals.

First, at step S401, it is judged if the amount of change of the ratio of the amount of intake air fed to the combustion chamber 2 and the amount of fuel fed to the combustion chamber 2 is less than a predetermined value. The amount of change of the ratio of the amount of intake air and the amount of fuel is for example calculated by the difference of the maximum value and minimum value of the ratio of the amount of intake air and the amount of fuel in a predetermined time. The amount of intake air is, for example, calculated based on the air flow rate detected by the air flow meter 102 and the engine speed detected by the crank angle sensor 108. Further, the above predetermined value at step S401 is determined in advance by experiments or calculations and is made the lower limit value of the amount of change of the ratio of the amount of intake air and the amount of fuel where it is estimated the fuel is being switched. Note that the amount of intake air may be calculated based on the pressure inside the intake passage, the opening degree of the throttle valve 9, etc. Further, step S401 is performed at a timing other than when switching the target air-fuel ratio, that is, at a time period in which the target air-fuel ratio is maintained constant. When at step S401 it is judged that the amount of change of the ratio of the intake air and the amount of fuel is less than a predetermined value, the present control routine proceeds to step S402.

In this case, it is considered that it is possible to obtain the desired precision of detection of the $SO_X$ concentration, so at step S402 the water concentration stability flag is set on. After this, the present control routine is ended. Therefore, in the present control routine, when the amount of change of the ratio of the amount of intake air and the amount of fuel is less than a predetermined value, it is judged that the concentration of water in the measured gas is stable.

On the other hand, when at step S401 it is judged that the amount of change of the ratio of the amount of intake air and the amount of fuel is a predetermined value or more, that is, when it is judged the fuel is being switched, at step S403, the water concentration stability flag is set off. After step S403, the present control routine is ended. Therefore, in the present control routine, when the amount of change of the ratio of the amount of intake air and the amount of fuel is a predetermined value or more, it is judged that the concentration of water in the measured gas is not stable.

Note that while details will not be explained, in the third embodiment, in a control routine separate from the control routine of the $SO_X$ concentration calculation processing and water concentration stability judgment processing, the amount of fuel fed to the combustion chamber 2 is controlled by feedback so that the air-fuel ratio detected by the air-fuel ratio sensor 104 becomes a target air-fuel ratio.

<Fourth Embodiment>

Below, a fourth embodiment of the present invention will be explained focusing on the parts different from the first embodiment to the third embodiment. In the fourth embodiment, in the same way as the first embodiment, the $SO_X$ detection system 1 shown in FIG. 2 is used to detect the concentration of $SO_X$ in the measured gas. Further, in the fourth embodiment, the ECU 80 judges if the fuel is being switched by a method different from the second embodiment and the third embodiment.

As explained above, if filling the fuel tank 33 with fuel, sometimes a different type of fuel from the fuel in the fuel tank 33 is filled. In this case, a predetermined time is required until the fuel of a mixture of the fuel which had been originally present inside the fuel tank 33 and the newly fed different fuel is switched with the fuel present in the piping from the fuel tank 33 to the fuel injector 3. That is, fuel is switched in the period from when fuel is filled to when the amount of fuel fed to the combustion chamber 2 reaches a predetermined value. Therefore, in the fourth embodiment, the ECU 80 judges that the fuel is being switched in the period from when the fuel tank 33 is filled with fuel to when the combustion chamber 2 is fed with a predetermined amount or more of fuel. Further, the ECU 80 judges that the concentration of water in the measured gas is not stable if it judges that the fuel is being switched.

<Control Routine of Water Concentration Stability Judgment Processing>

Figure 9:
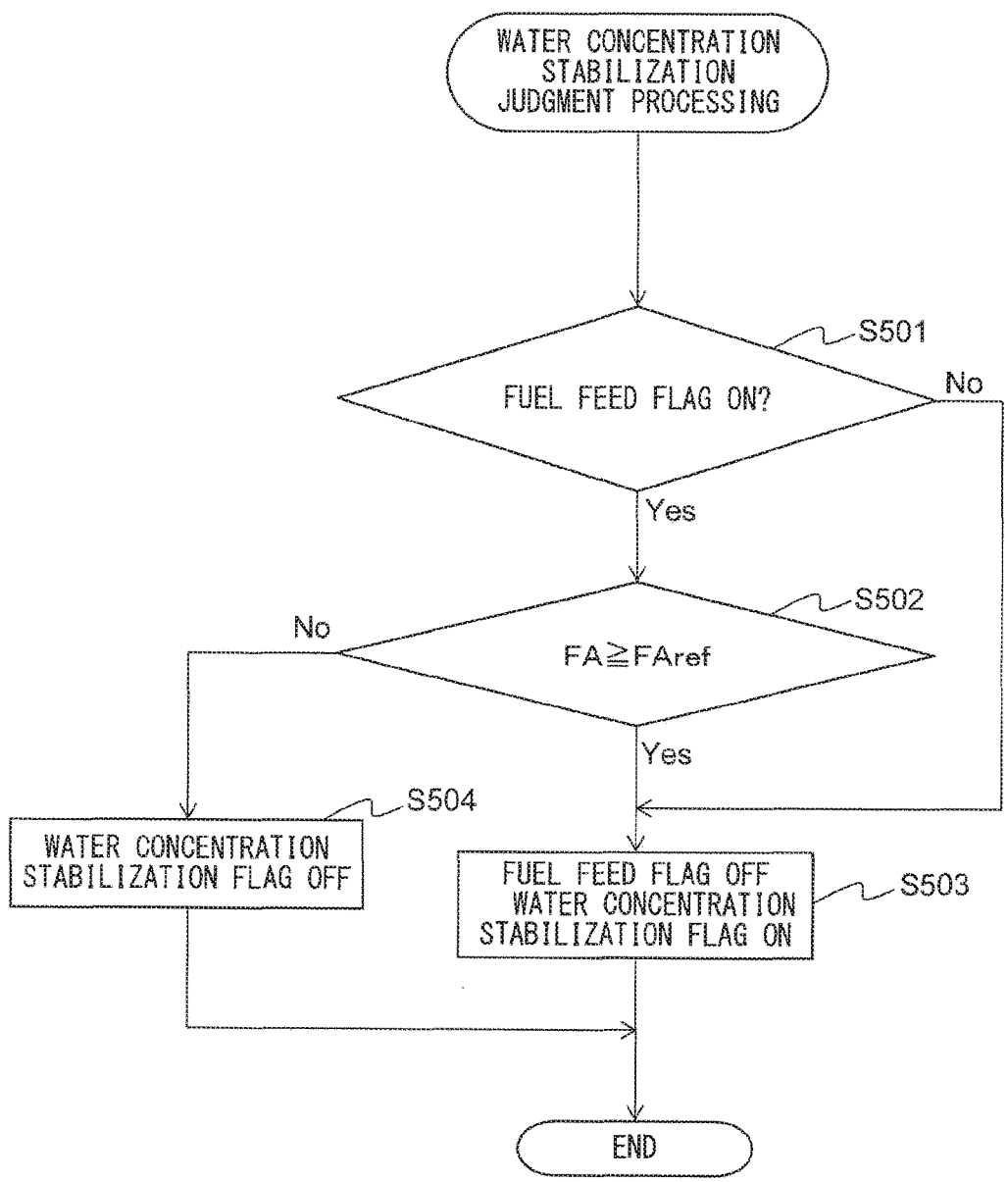
FIG. 9 is a flow chart showing a control routine of water concentration stability judgment processing in a fourth embodiment of the present invention.

In the fourth embodiment, as the control routine of water concentration stability judgment processing, the control routine shown in FIG. 9 is executed. FIG. 9 is a flow chart showing a control routine of water concentration stability judgment processing in a fourth embodiment of the present invention. The illustrated control routine is repeatedly performed by the ECU 80 at predetermined time intervals.

First, at step S501, it is judged if a fuel feed flag is on. The fuel feed flag is set on when the ECU 80 judges that the fuel tank 33 has been filled with fuel. The ECU 80 judges that the fuel tank 33 has been filled with fuel when, for example, a fuel feed port provided in the vehicle at which the internal combustion engine in which the $SO_X$ detection system 1 is used is opened. Further, the ECU 80 may judge that the fuel tank 33 has been filled with fuel when the amount of fuel in the fuel tank 33 detected by the fuel level sensor 107 has increased by a predetermined value or more. Note that the initial value of the fuel feed flag before fuel is first pumped into the fuel tank 33 is set to off.

When at step S501 it is judged that the fuel feed flag is on, the present control routine proceeds to step S502. At step S502, it is judged if after filling fuel, the fuel amount FA fed to the combustion chamber 2 is the reference fuel amount FAref or more. The reference fuel amount FAref is determined in advance by experiments or calculations and, for example, is made an amount of fuel able to be held between the fuel pump 19 and the fuel injector 3.

When at step S502 it is judged that the fuel amount FA is the reference fuel amount FAref or more, the present control routine proceeds to step S503. In this case, the fuel may not have finished being switched, so at step S503 the fuel feed flag is set off and the water concentration stability flag is set on. After this, the present control routine is ended. On the other hand, when at step S502 it is judged that the fuel amount FA is less than the reference fuel amount FAref, the present control routine proceeds to step S504. In this case, the fuel may not yet have finished being switched, so at step S504 the water concentration stability flag is set off. After this, the present control routine is ended.

Further, when at step S501 it is judged that the fuel feed flag is off, the present control routine proceeds to step S503. In this case, the fuel may finish being switched, so at step S503 the fuel feed flag is maintained off and the water concentration stability flag is set on. After this, the present control routine is ended.

Therefore, in the present control routine, when it is judged that a predetermined amount or more of fuel is fed to the combustion chamber 2 after the fuel tank 33 is filled with fuel, it is judged that the concentration of water in the measured gas is stable. On the other hand, in the present control routine, when a predetermined amount or more of fuel is not fed to the combustion chamber 2 after the fuel tank 33 is filled with fuel, it is judged that the concentration of water in the measured gas is not stable.

<Fifth Embodiment>

Below, a fifth embodiment of the present invention will be explained focusing on the parts different from the first embodiment to the fourth embodiment. In the fifth embodiment, in the same way as the first embodiment, the $SO_X$ detection system 1 shown in FIG. 2 is used to detect the concentration of $SO_X$ in the measured gas.

If the temperature of the exhaust gas falls to the dew point temperature or less, the water vapor in the exhaust gas condenses and condensed water is formed. If the internal combustion engine is started in the state where condensed water is present in the exhaust passage or EGR passage 14, the concentration of water in the exhaust gas rises while condensed water vaporizes due to engine warmup. Further, at the time of cold start of the internal combustion engine, sometimes the exhaust gas is cooled at the exhaust passage or EGR passage 14 and the water vapor in the exhaust gas condenses. In this case, the concentration of water in the exhaust gas decreases. Therefore, if there is condensed water present in at least one of the exhaust passage and EGR passage 14 or if condensed water will be formed in at least one of the exhaust passage and EGR passage 14, the concentration of water in the measured gas changes. Therefore, in the fifth embodiment, the ECU 80 judges that the concentration of water in the measured gas is not stable if it judges that there is condensed water present in at least one of the exhaust passage and EGR passage 14 or judges that condensed water will be formed in at least one of the exhaust passage and EGR passage 14.

<Control Routine of Water Concentration Stability Judgment Processing>

Figure 10:
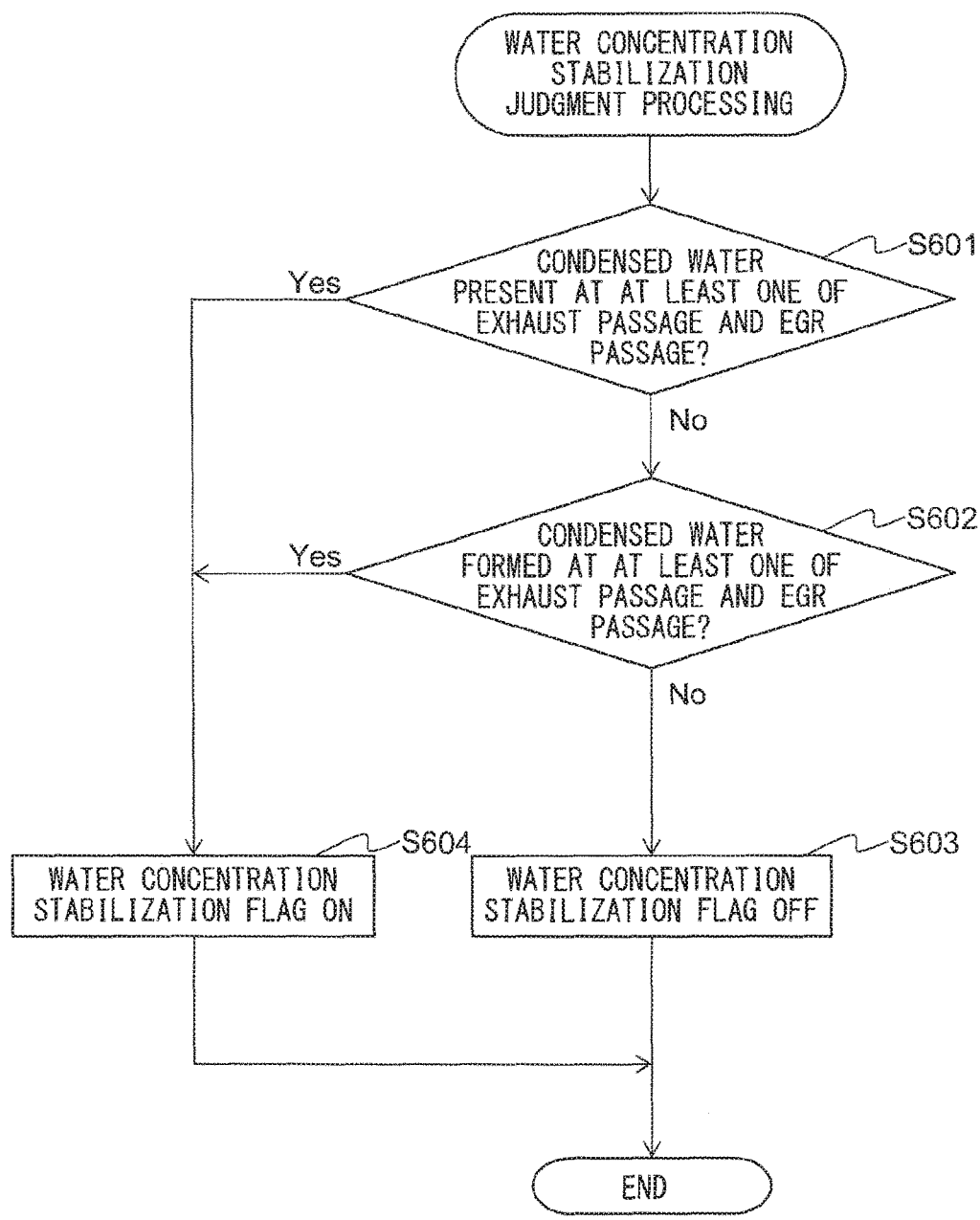
FIG. 10 is a flow chart showing a control routine of water concentration stability judgment processing in a fifth embodiment of the present invention.

In the fifth embodiment, as the control routine of water concentration stability judgment processing, the control routine shown in FIG. 10 is performed. FIG. 10 is a flow chart showing a control routine of water concentration stability judgment processing in a fifth embodiment of the present invention. The illustrated control routine is repeatedly performed by the ECU 80 at predetermined time intervals.

First, at step S601 it is judged if condensed water is present in at least one of the exhaust gas passage and EGR passage 14. When it is judged that condensed water is present in at least one of the exhaust gas passage and EGR passage 14, at step S604, the water concentration stability flag is set off. After step S604, the present control routine is ended. On the other hand, when at step S601 it is judged that there is no condensed water present in the exhaust gas passage and EGR passage 14, the present control routine proceeds to step S602.

At step S602, it is judged if condensed water will be formed in at least one of the exhaust gas passage and EGR passage 14. In other words, at step S602, it is judged if water vapor in the exhaust gas will condense when the exhaust gas passes through the exhaust gas passage and EGR passage 14. If at step S602 it is judged that condensed water will be formed in at least one of the exhaust gas passage and EGR passage 14, at step S604, the water concentration stability flag is set off. After step S604, the present control routine is ended. On the other hand, if at step S602 it is judged that condensed water will not be formed in the exhaust gas passage and EGR passage 14, the present control routine proceeds to step S603. In this case, it is considered that the desired precision of detection of the $SO_X$ concentration can be obtained, so at step S603, the water concentration stability flag is set on. After this, the present control routine is ended.

Therefore, in the present control routine, it is judged that the concentration of water in the measured gas is stable if it is judged that no condensed water is present in at least one of the exhaust gas passage and EGR passage 14 and it is judged that condensed water will not be formed in at least one of the exhaust gas passage and EGR passage 14. On the other hand, in the present control routine, it is judged that the concentration of water in the measured gas is not stable if it is judged that condensed water is present in at least one of the exhaust gas passage and EGR passage 14 or it is judged that condensed water will be formed in at least one of the exhaust gas passage and EGR passage 14.

Note that the judgments at step S601 and step S602 are, for example, performed by the known methods as described in Japanese Patent Publication No. 2009-222424A. Below, the judgment regarding the exhaust passage will be explained, but the judgment regarding the EGR passage 14 can be performed by a similar method.

The ECU 80 judges at step S601 the presence of any condensed water in the exhaust passage based on the estimated temperature at the inside wall of the exhaust passage, dew point temperature, and air flow rate detected by the air flow meter 102. The estimated temperature of the inside wall of the exhaust passage is calculated based on the air flow rate detected by the air flow meter 102, the exhaust temperature detected by the exhaust temperature sensor 105, and the outside air temperature detected by the outside air temperature sensor 109. Further, the dew point temperature is calculated based on the exhaust air-fuel ratio. The exhaust air-fuel ratio is calculated from the ratio of an amount of the intake air fed to the combustion chamber 2 and an amount of fuel fed to the combustion chamber 2 or is detected by the air-fuel ratio sensor 104. Note that the ECU 80 may judge the presence of any condensed water based on the previous operating state of the internal combustion engine, for example, the operating time of the internal combustion engine. Further, the ECU 80 may judge the presence of any condensed water based on the water temperature at the time of startup of the internal combustion engine. The water temperature is detected by the water temperature sensor 110.

Further, the ECU 80 judges at step S602 if condensed water will be formed in the exhaust passage based on the air flow rate detected by the air flow meter 102, the exhaust temperature detected by the exhaust temperature sensor 105, and the outside air temperature detected by the outside air temperature sensor 109.

Note that when the internal combustion engine in which the $SO_X$ detection system 1 is used is not provided with an EGR passage, at step S601 and step S602, only the exhaust passage is judged.

<Sixth Embodiment>

Below, a sixth embodiment of the present invention will be explained focusing on the parts different from the first embodiment to the fifth embodiment. In the sixth embodiment, in the same way as the first embodiment, the $SO_X$ detection system 1 shown in FIG. 2 is used to detect the concentration of $SO_X$ in the measured gas.

In an internal combustion engine in which an $SO_X$ detection system 1 is used, sometimes water or aqueous solution is injected in the path by which the measured gas reaches the device part 10 (below, referred to as "the measured gas path"). For example, in an internal combustion engine provided with a turbocharger, sometimes water is injected into the intake passage for lowering the temperature of the intake air. Further, in a diesel engine provided with an SCR catalyst, sometimes a urea aqueous solution is injected into the exhaust passage for producing ammonia to remove the NOx by reduction. If water or aqueous solution is injected into the measured gas path, vaporization of the injected water or aqueous solution is liable to cause the concentration of water in the measured gas to change. Therefore, in the sixth embodiment, the ECU 80 judges that the concentration of water in the measured gas is not stable in the period from when the water or aqueous solution is injected into the measured gas path to when the injected water or aqueous solution passes the device part 10 in the exhaust passage.

Note that the measured gas path includes the intake passage, the exhaust passage at the upstream side of the device part 10 in the exhaust flow direction, and the EGR passage 14. Further, when the EGR passage 14 is connected to the downstream side of the device part 10 in the exhaust flow direction, the measured gas path includes the intake passage, exhaust passage at the upstream side of the EGR passage 14 in the exhaust flow direction, and the EGR passage 14.

<Control Routine of Water Concentration Stability Judgment Processing>

Figure 11:
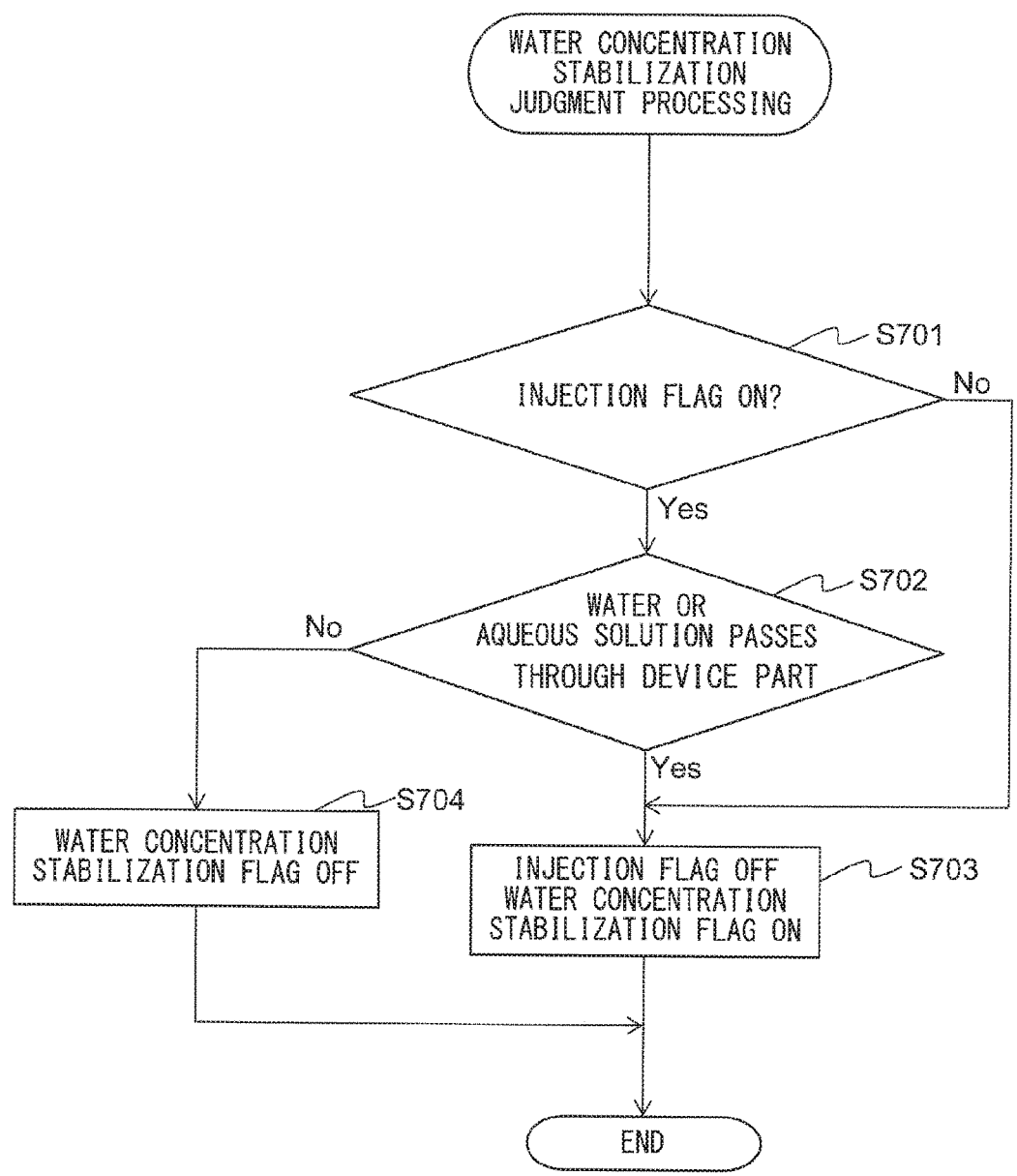
FIG. 11 is a flow chart showing a control routine of water concentration stability judgment processing in a sixth embodiment of the present invention.

In the sixth embodiment of the present invention, as the control routine of water concentration stability judgment processing, the control routine shown in FIG. 11 is performed. FIG. 11 is a flow chart showing a control routine of water concentration stability judgment processing in a sixth embodiment of the present invention. The illustrated control routine is repeatedly performed by the ECU 80 at predetermined time intervals.

First, at step S701, it is judged if the injection flag is on. The injection flag is set on when the water or aqueous solution is injected in the measured gas path by control by the ECU 80. Note that the initial value of the injection flag before the water or aqueous solution is first injected is set off. If at step S701 it is judged that the injection flag is on, the present control routine proceeds to step S702.

At step S702, it is judged if the water or aqueous solution injected in the measured gas path has passed the device part 10 in the exhaust passage. Specifically, the ECU 80 calculates the passage time Tar from when the water or aqueous solution is injected to when the injected water or aqueous solution passes the device part 10 in the exhaust passage. The passage time Tar is, for example, calculated based on a map shown as a function of the air flow rate detected by the air flow meter 102 and the water temperature detected by the water temperature sensor 110. Specifically, in the above map, it is shown that the passage time Tar becomes shorter the higher the air flow rate and it is shown that it becomes shorter the higher the water temperature. Note that instead of the water temperature, the oil temperature may be used. The ECU 80 judges that the water or aqueous solution injected in the measured gas path has passed the device part 10 in the exhaust passage when the time elapsed after injecting the water or aqueous solution is the passage time Tar or more. On the other hand, the ECU 80 judges that the water or aqueous solution injected in the measured gas path has not passed the device part 10 in the exhaust passage if the elapsed time after injecting the water or aqueous solution is less than the passage time Tar.

When at step S702 it is judged that the water or aqueous solution injected in the measured gas path has passed through the device part 10 in the exhaust passage, at step S703, the injection flag is set to OFF and the water concentration stability flag is set to ON. After this, the present control routine is ended. On the other hand, when at step S702 it is judged that the water or aqueous solution injected in the measured gas path has not passed through the device part 10 in the exhaust passage, at step S704, the water concentration stability flag is set off. After this, the present control routine is ended.

Further, when at step S701 it is judged that the injection flag is off, at step S703 the injection flag is maintained off and the water concentration stability flag is set on. After this, the present control routine is ended.

Therefore, in the present control routine, if it is judged that the water or aqueous solution injected in the measured gas path has passed through the device part 10 in the exhaust passage or if the water or aqueous solution is not injected in the measured gas path, it is judged that the concentration of water in the measured gas is stable. On the other hand, in the present control routine, if it is judged that the water or aqueous solution injected in the measured gas path is not passing through the device par 10 of the exhaust passage, it is judged that the concentration of water in the measured gas is not stable.

<Seventh Embodiment>

Below, a seventh embodiment of the present invention will be explained focusing on the parts different from the first embodiment to the sixth embodiment. In the seventh embodiment, in the same way as first embodiment, the $SO_X$ detection system 1 shown in FIG. 2 is used to detect the concentration of $SO_X$ in the measured gas.

As explained above, if applying a predetermined voltage of the decomposition start voltage of water or more across the first electrode 41 and the second electrode 42 of the first electrochemical cell 51, the decomposition current of water flows between the electrodes. If this decomposition current of water is changing, it is deduced that the concentration of water in the measured gas also is changing. Therefore, in the seventh embodiment, the ECU 80 controls the first power supply 61 so that a voltage of the decomposition start voltage of water or more is applied between the first electrode 41 and the second electrode 42 of the first electrochemical cell 51 and judges that the concentration of water in the measured gas is not stable if the amount of change of the inter-electrode current detected by the first ammeter 62 is a predetermined value or more.

<Control Routine of Water Concentration>Stability Judgment Processing

Figure 12:
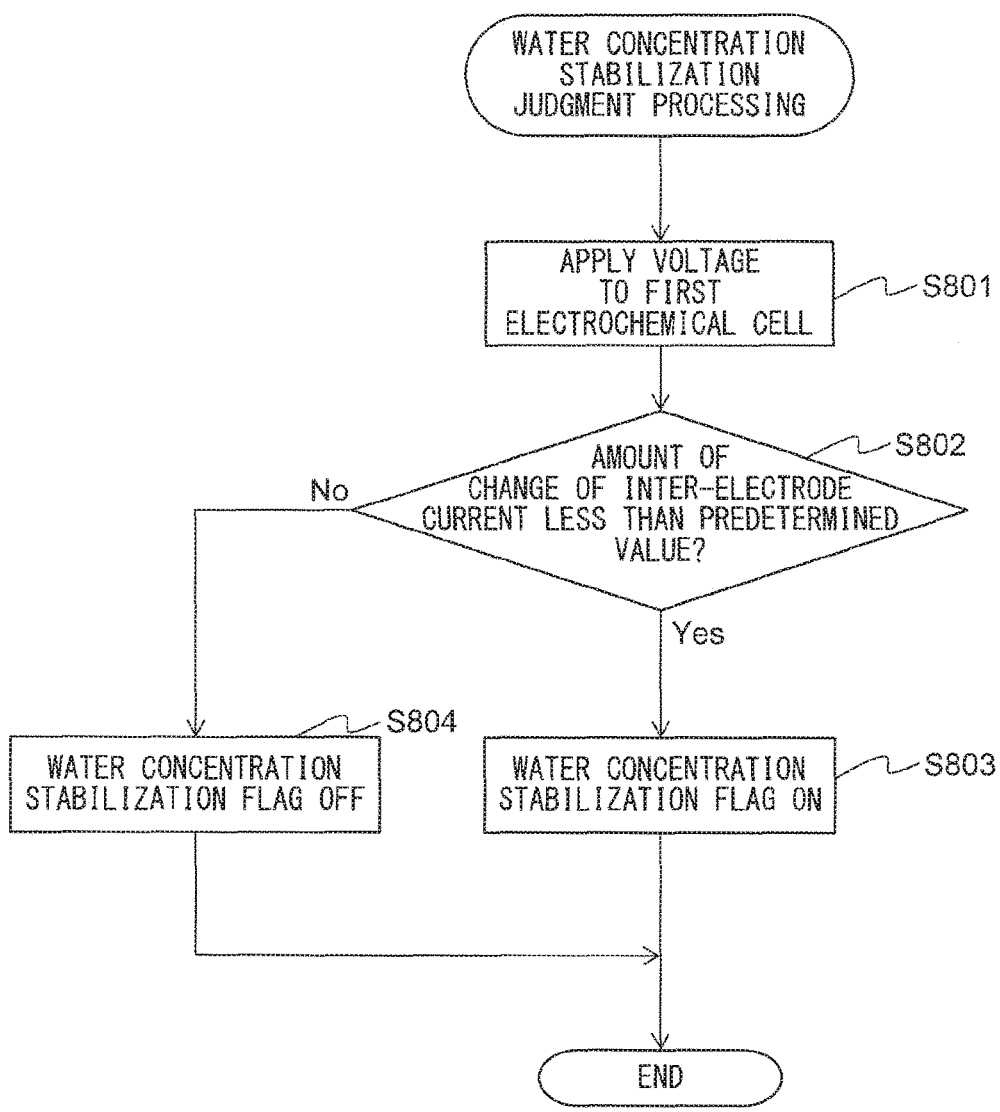
FIG. 12 is a flow chart showing a control routine of water concentration stability judgment processing in a seventh embodiment of the present invention.

In the seventh embodiment of the present invention, as the control routine of water concentration stability judgment processing, the control routine shown in FIG. 12 is performed. FIG. 12 is a flow chart showing a control routine of water concentration stability judgment processing in the seventh embodiment of the present invention. The illustrated control routine is repeatedly performed by the ECU 80 at predetermined time intervals.

First, at step S801, a voltage of the decomposition start voltage of water or more is applied between the first electrode 41 and the second electrode 42 of the first electrochemical cell 51. The applied voltage is set to a voltage of 0.6V to less than 2.0V, for example, 1.1V.

Next, at step S802, it is judged if the amount of change of the inter-electrode current detected by the first ammeter 62 is less than a predetermined value. The amount of change of the inter-electrode current is for example calculated by the difference of a maximum value and a minimum value of the inter-electrode current in a predetermined time. Further, the predetermined value at step S802 is determined in advance by experiments or calculations and is made a value corresponding to the lower limit value of the amount of change of the water concentration by which it was difficult to obtain the desired precision of calculation of the $SO_X$ concentration.

When at step S802 it is judged that the amount of change of the inter-electrode current is less than a predetermined value, at step S803, the water concentration stability flag is set on. After this, the present control routine is ended. Therefore, in the present control routine, when the amount of change of the inter-electrode current is less than a predetermined value, it is judged that the concentration of water in the measured gas is stable. On the other hand, when the amount of change of the inter-electrode current is a predetermined value or more, at step S804, the water concentration stability flag is set off. After this, the present control routine is ended. Therefore, in the present control routine, when the amount of change of the inter-electrode current is a predetermined value or more, it is judged that the concentration of water in the measured gas is not stable.

Note that, at step S802, as a current correlation parameter correlated with the inter-electrode current, a parameter other than the current value such as the resistance value may be detected. The current correlation parameter is detected by any detector which the $SO_X$ detection system 1 is provided with and acquired by the ECU 80. In this case, at step S802, it is judged if the amount of change of the inter-electrode current parameter is less than a predetermined value.

Further, as explained above, the decomposition start voltage of $SO_X$ is the same extent as the decomposition start voltage of water or lower than that. For this reason, if at step S801 a voltage of the decomposition start voltage of water or more is applied to the first electrochemical cell 51, the $SO_X$ contained in the measured gas also is decomposed. In this case, when at step S803 the water concentration stability flag is set on, the amount of the decomposition products of the $SO_X$ adsorbed on the first electrode 41 may become substantially saturated. For this reason, in the seventh embodiment, in the control routine of $SO_X$ concentration calculation processing of FIG. 5, steps S104 and S105 are omitted. Along with this, step S108 and step S110 are also omitted. Further, in the seventh embodiment, to judge if the concentration of water in the measured gas is stable, it is necessary to apply a voltage of the decomposition start voltage of water or more to the first electrochemical cell 51. For this reason, step S109 of FIG. 5 is also omitted.

<Eighth Embodiment>

Below, an eighth embodiment of the present invention will be explained focusing on the parts different from the first embodiment to the seventh embodiment. In the eighth embodiment, the $SO_X$ detection system 1a shown in FIG. 13A and FIG. 13B is used to detect the concentration of $SO_X$ in the measured gas.

<Explanation of $SO_X$ Detection System>

Figure 13A:
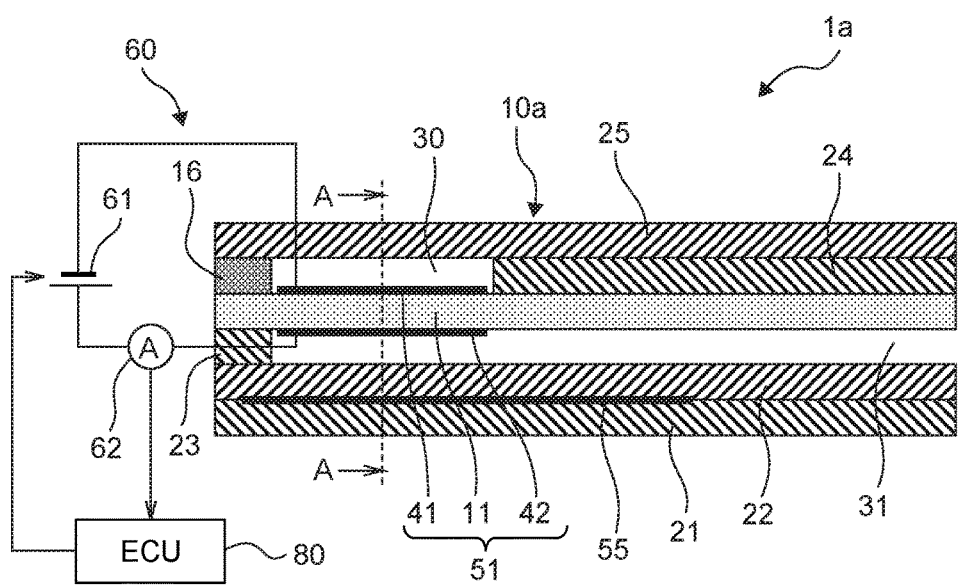
FIG. 13A and FIG. 13B are schematic cross-sectional views showing the configuration of an $SO_X$ detection system according to an eighth embodiment of the present invention.
Figure 13B:
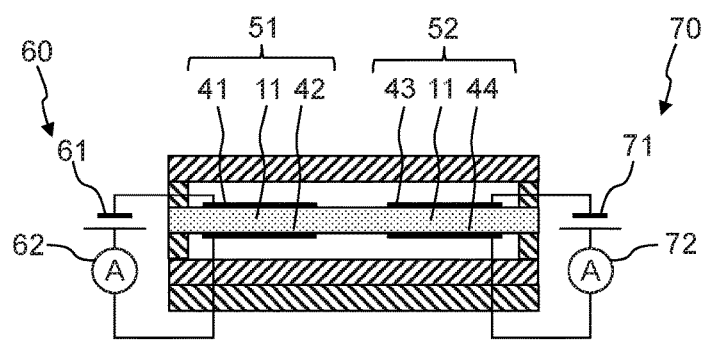

FIG. 13A is a schematic cross-sectional view showing the configuration of the $SO_X$ detection system 1a according to the eighth embodiment of the present invention. FIG. 13B is a cross-sectional view along the line A-A of FIG. 13A. The $SO_X$ detection system 1a comprises a device part 10a, a first circuit 60 and a second circuit 70 connected to the device part 10a, and an ECU 80. The device part 10a is configured similar to the device part 10 in the first embodiment except for the point of providing the second electrochemical cell 52 in addition to the first electrochemical cell 51. As will be understood from FIG. 13A and FIG. 13B, the second electrochemical cell 52 is arranged along with the first electrochemical cell 51 so that the distance from the diffusion regulating layer 16 becomes equal to the first electrochemical cell 51.

The device part 10a further comprises a third electrode 43 and a fourth electrode 44. The third electrode 43 is arranged on the surface of the first solid electrolyte layer 11 at the measured gas chamber 30 side. Therefore, the third electrode 43 is exposed to the measured gas in the measured gas chamber 30. The third electrode 43 has a surface area the same as the first electrode 41. Further, the third electrode 43 is arranged aligned with the first electrode 41 so that the distance from the diffusion regulating layer 16 becomes equal to the first electrode 41. On the other hand, the fourth electrode 44 is arranged on the surface of the first solid electrolyte layer 11 at the first atmospheric chamber 31 side. Therefore, the fourth electrode 44 is exposed to the gas (atmospheric air) inside the first atmospheric chamber 31. The fourth electrode 44 has a surface area the same as the second electrode 42. Further, the fourth electrode 44 is arranged aligned with the second electrode 42 so that the distance from the diffusion regulating layer 16 becomes equal to the second electrode 42. The third electrode 43 and the fourth electrode 44 are arranged so as to face each other across the first solid electrolyte layer 11. The third electrode 43, first solid electrolyte layer 11, and fourth electrode 44 form the second electrochemical cell 52.

In the present embodiment, the material forming the third electrode 43 includes platinum (Pt), gold (Au), lead (Pb), silver (Ag), or other metal element or alloy of these as a main ingredient. Preferably, the third electrode 43 is a porous cermet electrode containing at least one of platinum (Pt), gold (Au), lead (Pb), and silver (Ag) as a main ingredient. Further, the fourth electrode 44 is a porous cermet electrode containing platinum (Pt) as a main ingredient. Note that the material forming the third electrode 43 is not necessarily limited to the above material. It may be any material so long as the electrode is configured so that the speed of decomposition of $SO_X$ becomes lower compared with the first electrode 41. In particular, in the present embodiment, the material forming the third electrode 43 is preferably a material where the speed of decomposition of $SO_X$ in the third electrode 43 becomes zero. Further, the material forming the fourth electrode 44 is not necessarily limited to the above material. It may be any material so long as when a predetermined voltage is applied across the third electrode 43 and the fourth electrode 44, it can make oxide ions move between the third electrode 43 and the fourth electrode 44.

Note that in the example shown in FIG. 13A and FIG. 13B, the second electrochemical cell 52 shares the first solid electrolyte layer 11 with the first electrochemical cell 51. However, the second electrochemical cell 52 may comprise a solid electrolyte layer separate from the first solid electrolyte layer 11 forming the first electrochemical cell 51.

The second circuit 70 comprises a second power supply 71 and a second ammeter 72. The second power supply 71 applies a voltage between the third electrode 43 and the fourth electrode 44 so that the potential of the fourth electrode 44 becomes higher than the potential of the third electrode 43. The output port 86 of the ECU 80 is connected through a corresponding drive circuit 88 to the second power supply 71. Therefore, the ECU 80 can control the second power supply 71 to control the voltage applied across the third electrode 43 and the fourth electrode 44.

The second ammeter 72 detects the current flowing between the third electrode 43 and the fourth electrode 44 (that is, the current flowing through the inside of the first solid electrolyte layer 11), that is, the inter-electrode current. The output of the second ammeter 72 is input to the input port 85 of the ECU 80 through a corresponding AD converter 87. Therefore, the ECU 80 can acquire the inter-electrode current detected by the second ammeter 72 from the second ammeter 72.

In the second electrochemical cell 52, even if a voltage of the decomposition start voltage of water or more is applied, the $SO_X$ will not be decomposed much at all. For this reason, the inter-electrode current in the second electrochemical cell 52 is not affected much at all due to the decomposition of the $SO_X$. Therefore, the second electrochemical cell 52 can detect the concentration of water in the measured gas more preciously than the first electrochemical cell 51. Therefore, in the eighth embodiment, the ECU 80 controls the second power supply so that a voltage of the decomposition start voltage of water or more is applied across the third electrode 43 and the fourth electrode 44 of the second electrochemical cell 52 and judges that the concentration of water in the measured gas is not stable if the amount of change of the inter-electrode current detected by the second ammeter 72 is a predetermined value or more.

<Control Routine of Water Concentration Stability Judgment Processing>

In the eighth embodiment of the present invention, as the control routine of water concentration stability judgment processing, the control routine shown in FIG. 14 is performed. FIG. 14 is a flow chart showing a control routine of water concentration stability judgment processing in an eighth embodiment of the present invention. The illustrated control routine is repeatedly performed by the ECU 80 at predetermined time intervals.

First, at step S901, a voltage of the decomposition start voltage of water or more is applied between the third electrode 43 and the fourth electrode 44 of the second electrochemical cell 52. The applied voltage is set to a voltage of 0.6V to less than 2.0V, for example, 1.1V.

Next, at step S902, it is judged if the amount of change of the inter-electrode current detected by the second ammeter 72 is less than a predetermined value. The amount of change of the inter-electrode current is, for example, calculated by the difference of a maximum value and a minimum value of the inter-electrode current at a predetermined time. Further, the above predetermined value at at step S902 is determined in advance by experiments or calculations and is made a value corresponding to the lower limit value of the amount of change of the water concentration by which obtaining the desired precision of calculation of the $SO_X$ concentration is difficult.

When at step S902 it is judged that the amount of change of the inter-electrode current is less than a predetermined value, at step S903, the water concentration stability flag is set on. After this, the present control routine is ended. Therefore, in the present control routine, when the amount of change of the inter-electrode current is less than a predetermined value, it is judged that the concentration of water in the measured gas is stable. On the other hand, when it is judged that the amount of change of the inter-electrode current is a predetermined value or more, at step S904, the water concentration stability flag is set off. After this, the present control routine is ended. Therefore, in the present control routine, when the amount of change of the inter-electrode current is a predetermined value or more, it is judged that the concentration of water in the measured gas is not stable.

Note that, at step S902, as the current correlation parameter correlated with the inter-electrode current, a parameter other than the current value such as the resistance value may be detected. The current correlation parameter is detected by any detector which the $SO_X$ detection system 1a is provided with and is acquired by the ECU 80. In this case, at step S902, it is judged if the amount of change of the inter-electrode current parameter is less than a predetermined value.

Further, in the eighth embodiment, the control routine of $SO_X$ concentration calculation processing of FIG. 5 may be changed as follows: At step S104, not only the first electrochemical cell 51, but also the second electrochemical cell 52 is supplied with a voltage of the decomposition start voltage of water or more. The voltage applied to the first electrochemical cell 51 and the second electrochemical cell 52 is set to a voltage of 0.6V to less than 2.0V, for example, 1.1V. After this, at step S106, the inter-electrode current flowing between the first electrode 41 and the second electrode 42 of the first electrochemical cell 51 and the inter-electrode current flowing between the third electrode 43 and the fourth electrode 44 of the second electrochemical cell 52 are detected. Next, at step S107, a map is used to calculate the concentration of $SO_X$ in the measured gas based on the difference between the inter-electrode current flowing between the first electrode 41 and the second electrode 42 and the inter-electrode current flowing between the third electrode 43 and the fourth electrode 44. In this map, it is shown that the concentration of $SO_X$ in the measured gas becomes higher the larger the difference of the inter-electrode current. By using the above-mentioned method to calculate the $SO_X$ concentration, the effect of the inter-electrode current generated due to decomposition of oxygen and water can be decreased, so it is possible to further improve the precision of detection of the $SO_X$ concentration. Note that, at step S106, as the current correlation parameter correlated with the inter-electrode current, a parameter other than the current value such as the resistance value may be detected. In this case, the difference of current correlation parameters is used as the basis to calculate the concentration of $SO_X$ in the measured gas at step S107.

Note that, instead of the control routine shown in FIG. 14, any one of the control routines shown in FIG. 6 to FIG. 12 may be executed using the $SO_X$ detection system 1a. Furthermore, several of the control routines shown in FIG. 6 to FIG. 12 may be performed together.

<Ninth Embodiment>

Below, a ninth embodiment of the present invention will be explained focusing on the parts different from the first embodiment to the eighth embodiment. In the ninth embodiment, the $SO_X$ detection system 1b shown in FIG. 15 is used to detect the concentration of $SO_X$ in the measured gas.

<Explanation of $SO_X$ Detection System>

Figure 15:
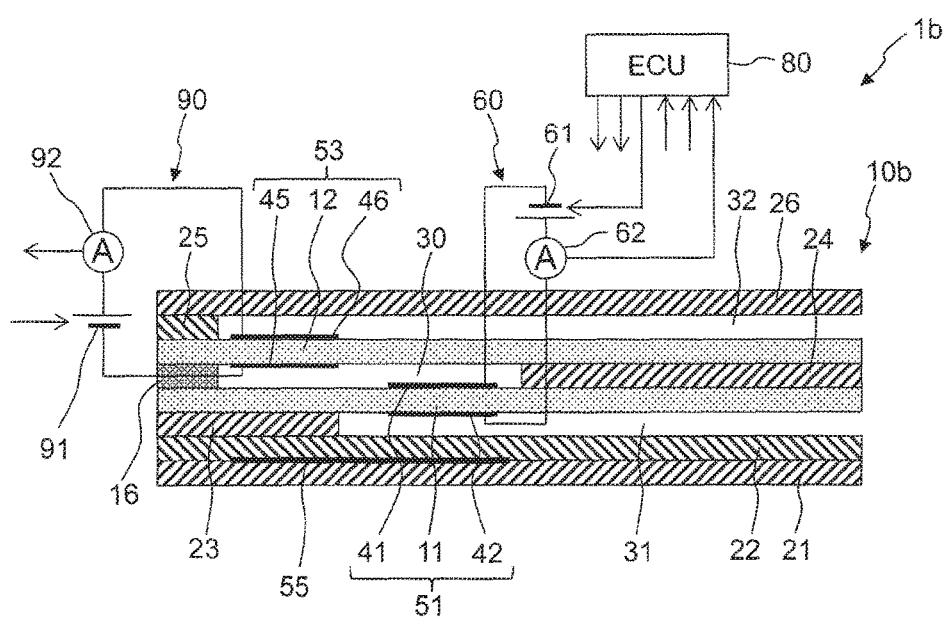
FIG. 15 is a schematic cross-sectional view showing the configuration of an $SO_X$ detection system according to a ninth embodiment of the present invention.

FIG. 15 is a schematic cross-sectional view showing the configuration of an $SO_X$ detection system 1b according to a ninth embodiment of the present invention. The $SO_X$ detection system 1b comprises a device part 10b, a first circuit 60 and a third circuit 90 connected to the device part 10b, and an ECU 80. The device part 10b is configured in the same way as the device part 10 in the first embodiment except for the point of being provided with not only the first electrochemical cell 51, but also the third electrochemical cell 53.

As shown in FIG. 15, the device part 10b is comprised of a plurality of layers. Specifically, the device part 10b comprises a first solid electrolyte layer 11, second solid electrolyte layer 12, diffusion regulating layer 16, first barrier layer 21, second barrier layer 22, third barrier layer 23, fourth barrier layer 24, fifth barrier layer 25, and sixth barrier layer 26.

The second solid electrolyte layer 12 is configured similar to the first solid electrolyte layer 11. The sixth barrier layer 26 is configured in the same way as the first barrier layer 21 to the fifth barrier layer 25. The layers of the device part 10b are stacked in the order, from the bottom of FIG. 15, of the first barrier layer 21, second barrier layer 22, third barrier layer 23, first solid electrolyte layer 11, diffusion regulating layer 16 and fourth barrier layer 24, second solid electrolyte layer 12, fifth barrier layer 25, and sixth barrier layer 26.

The first solid electrolyte layer 11, second solid electrolyte layer 12, diffusion regulating layer 16, and fourth barrier layer 24 define and form the measured gas chamber 30. Note that the measured gas chamber 30 may be configured in any way so long as it adjoins the first solid electrolyte layer 11 and the second solid electrolyte layer 12 and is configured so that the measured gas flows into it.

The second solid electrolyte layer 12, fifth barrier layer 25, and sixth barrier layer 26 define and form the second atmospheric chamber 32. As will be understood from FIG. 15, the second atmospheric chamber 32 is arranged across the second solid electrolyte layer 12 at the opposite side from the measured gas chamber 30. The second atmospheric chamber 32 is opened to the atmospheric air at the outside of the exhaust passage. Therefore, atmospheric air flows into the second atmospheric chamber 32 as well. Note that the second atmospheric chamber 32 may be configured in any way so long as it adjoins the second solid electrolyte layer 12 and is configured so that atmospheric air flows into it.

The device part 10b further comprises a fifth electrode 45 and sixth electrode 46. The fifth electrode 45 is arranged on the surface of the second solid electrolyte layer 12 at the measured gas chamber 30 side. Therefore, the fifth electrode 45 is exposed to the measured gas in the measured gas chamber 30. Further, the fifth electrode 45 is arranged in the measured gas chamber 30 away from the first electrode 41 at the diffusion regulating layer 16 side. Therefore, the measured gas flowing into the measured gas chamber through the diffusion regulating layer 16 first flows around the fifth electrode 45, then flows around the first electrode 41. On the other hand, the sixth electrode 46 is arranged on the surface of the second solid electrolyte layer 12 at the second atmospheric chamber 32 side. Therefore, the sixth electrode 46 is exposed to the gas (atmospheric air) in the second atmospheric chamber 32. The fifth electrode 45 and the sixth electrode 46 are arranged facing each other across the second solid electrolyte layer 12. The fifth electrode 45, second solid electrolyte layer 12, and sixth electrode 46 form the third electrochemical cell 53.

The fifth electrode 45 and sixth electrode 46 are porous cermet electrodes including platinum (Pt) as main ingredients. However, the material forming the fifth electrode 45 is not necessarily limited to the above materials and may be any material so long as when applying a predetermined voltage between the fifth electrode 45 and the sixth electrode 46, it can decompose by reduction the oxygen contained in the measured gas in the measured gas chamber 30. Further, the material forming the sixth electrode 46 is not necessarily limited to the above materials and may be any material so long as when applying a predetermined voltage between the fifth electrode 45 and the sixth electrode 46, it can make oxide ions move between the fifth electrode 45 and the sixth electrode 46.

Note that, in the above embodiments, the third electrochemical cell 53 is configured including a second solid electrolyte layer 12 different from the first solid electrolyte layer 11 forming the first electrochemical cell 51. However, the first solid electrolyte layer and the second solid electrolyte layer may be the same solid electrolyte layer. That is, the first solid electrolyte layer 11 of FIG. 15 may be configured to also function as the second solid electrolyte layer and therefore the third electrochemical cell 53 may include the first solid electrolyte layer 11. In this case, the fifth electrode 45 is arranged on the surface of the first solid electrolyte layer 11 at the measured gas chamber 30 side, while the sixth electrode 46 is arranged on the surface of the first solid electrolyte layer 11 at the first atmospheric chamber 31 side.

The third circuit 90 comprises a third power supply 91 and a third ammeter 92. The third power supply 91 applies voltage across the fifth electrode 45 and the sixth electrode 46 so that the potential of the sixth electrode 46 becomes higher than the potential of the fifth electrode 45. The output port 86 of the ECU 80 is connected through a corresponding drive circuit 88 to the third power supply 91. Therefore, the ECU 80 can control the third power supply 91 to control the voltage applied across the fifth electrode 45 and the sixth electrode 46.

The third ammeter 92 detects the current flowing between the fifth electrode 45 and the sixth electrode 46 (that is, the current flowing through the inside of the second solid electrolyte layer 12), that is, the inter-electrode current. The output of the third ammeter 92 is input through a corresponding AD converter 87 to the input port 85 of the ECU 80. Therefore, the ECU 80 can acquire the inter-electrode current detected by the third ammeter 92 from the third ammeter 92.

<Pump Cell>

In the first electrochemical cell 51, as explained above, it is possible to apply a predetermined voltage of the decomposition start voltage of $SO_X$ and water or more across the first electrode 41 and the second electrode 42 to cause the water and $SO_X$ to be decomposed on the first electrode 41 and detect the inter-electrode current accompanying decomposition of water. However, if the measured gas reaching the first electrochemical cell 51 contains oxygen, oxygen is decomposed (ionized) on the first electrode 41 and the oxide ions generated due to this flow from the first electrode 41 to the second electrode 42. If decomposition current ends up flowing between the first electrode 41 and the second electrode 42 along with decomposition of oxygen, it becomes difficult to accurately detect the concentration of $SO_X$ based on the inter-electrode current.

Here, if applying a voltage within the limit current region of oxygen to the third electrochemical cell 53, the speed of conduction of the oxide ions able to be conducted by the third electrochemical cell 53 becomes faster than the speed of introduction of oxygen introduced through the diffusion regulating layer 16 to the inside of the measured gas chamber 30. Therefore, if voltage within the limit current region of oxygen is applied to the third electrochemical cell 53, almost all of the oxygen contained in the measured gas flowing through the diffusion regulating layer 16 to the inside of the measured gas chamber 30 can be removed.

Therefore, in the ninth embodiment, when using the first electrochemical cell 51 to detect the concentration of $SO_X$ in the measured gas, a voltage in the limit current region of oxygen is applied to the third electrochemical cell 53 arranged at the diffusion regulating layer 16 side from the first electrochemical cell 51. The limit current region of oxygen is a region of the lower limit voltage (for example, 0.1V) or more where the inter-electrode current does not change much at all even if raising the applied voltage by that amount or more. Further, the voltage applied to the third electrochemical cell 53 is made a voltage less than the decomposition start voltage of $SO_X$ and water (about 0.6V). Due to this, in the third electrochemical cell 53, it is possible to decompose and remove the oxygen without decomposing the water and $SO_X$. Therefore, the third electrochemical cell 53 functions as a pump cell discharging oxygen from the inside of the measured gas chamber 30 without discharging water and $SO_X$.

<Control Routine of $SO_X$ Concentration Calculation Processing>

In the ninth embodiment, the control routine of the $SO_X$ concentration calculation processing of FIG. 5 is changed in the following way. At step S104, voltage is applied to the third electrochemical cell 53 in addition to the first electrochemical cell 51. The voltage applied to the first electrochemical cell 51 is set to a voltage of 0.6V to less than 2.0V, for example, 1.1V. On the other hand, the voltage applied to the third electrochemical cell 53 is set to a voltage of 0.1V to less than 0.6V, for example, 0.4V. Due to this, the oxygen in the measured gas is removed at the third electrochemical cell 53 before the measured gas reaches the first electrochemical cell 51, so it is possible to further improve the precision of detection of the $SO_X$ concentration at the first electrochemical cell 51. Note that, at step S109, the voltage applied to the third electrochemical cell 53 in addition to the first electrochemical cell 51 may also be made zero or lowered.

Further, in the ninth embodiment, as a control routine of water concentration stability judgment processing, any one of the control routines shown in FIG. 6 to FIG. 12 is performed. Furthermore, a combination of several of the control routines shown in FIG. 6 to FIG. 12 may be performed.

Note that, as explained above, by applying voltage of the lower limit voltage of the limit current region of oxygen or more to the third electrochemical cell 53, the oxygen included in the measured gas is decomposed at the fifth electrode 45, and the oxide ions generated due to this decomposition are discharged from the measured gas chamber 30 to the second atmospheric chamber 32. At this time, by detecting the inter-electrode current flowing between the fifth electrode 45 and the sixth electrode 46 by the third ammeter 92, it is possible to detect the concentration of oxygen in the measured gas. Therefore, the third electrochemical cell 53 can be used as an air-fuel ratio sensor for detecting the exhaust air-fuel ratio. For this reason, if using the $SO_X$ detection system 1*b* to calculate the $SO_X$ concentration, instead of the air-fuel ratio sensor 104, the third electrochemical cell 53 can be used to detect the exhaust air-fuel ratio.

<Tenth Embodiment>

Below, a tenth embodiment of the present invention will be explained focusing on the parts different from the first embodiment to the ninth embodiment. In the tenth embodiment, the $SO_X$ detection system 1*c* shown in FIG. 16A and FIG. 16B is used to detect the concentration of $SO_X$ in the measured gas.

<Explanation of $SO_X$ Detection System>

Figure 16A:
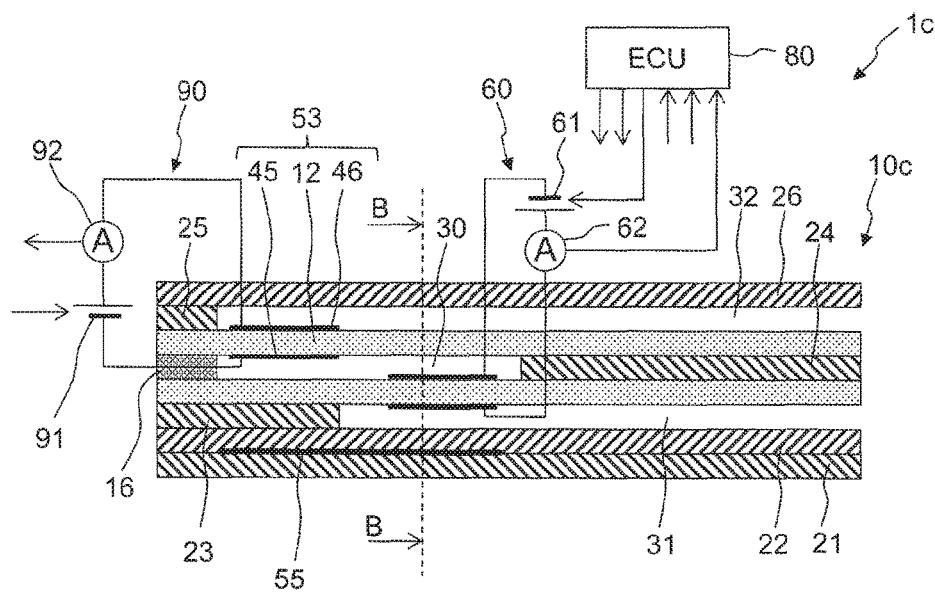
FIG. 16A and FIG. 16B are schematic cross-sectional views showing the configuration of an $SO_X$ detection system according to a tenth embodiment of the present invention.
Figure 16B:
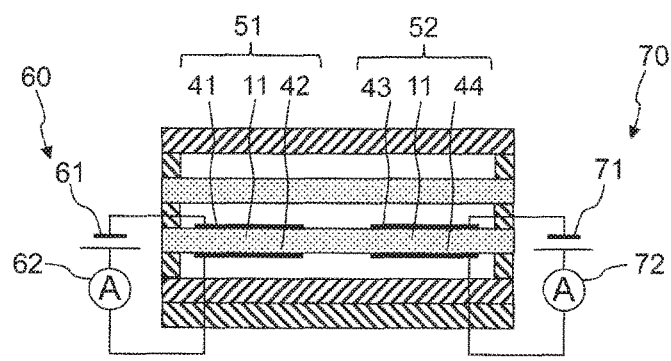

FIG. 16A and FIG. 16B is a schematic cross-sectional view showing the configuration of the $SO_X$ detection system 1*c* according to the tenth embodiment of the present invention. The $SO_X$ detection system 1*c* comprises a device part 10*c*, first circuit 60, second circuit 70, and third circuit 90 connected to the device part 10*c*, and an ECU 80. The device part 10*c* is configured in the same way as the device part 10*b* in the ninth embodiment except for the point of the second electrochemical cell 52 being provided in addition to the first electrochemical cell 51 and the third electrochemical cell 53. Further, the second electrochemical cell 52 of the device part 10*c* is configured in the same way as the second electrochemical cell 52 of the device part 10*a* shown in FIG. 13A and FIG. 13B. For this reason, a detailed explanation of the $SO_X$ detection system 1*c* will be omitted.

<Control Routine of $SO_X$ Concentration Calculation Processing>

In the tenth embodiment, the control routine of $SO_X$ concentration calculation processing of FIG. 5 is changed in the following way. At step S104, voltage is applied to not only the first electrochemical cell 51 but also the second electrochemical cell 52 and the third electrochemical cell 53. The voltage applied to the first electrochemical cell 51 and the second electrochemical cell 52 is set to a voltage of 0.6V to less than 2.0V, for example, 1.1V. On the other hand, the voltage applied to the third electrochemical cell 53 is set to a voltage of 0.1V to less than 0.6V, for example, 0.4V.

After this, at step S106, the inter-electrode current flowing between the first electrode 41 and the second electrode 42 of the first electrochemical cell 51 and the inter-electrode current flowing between the third electrode 43 and the fourth electrode 44 of the second electrochemical cell 52 are detected. Next, at step S107, a map is used to calculate the concentration of $SO_X$ in the measured gas based on the difference between the inter-electrode current flowing between the first electrode 41 and the second electrode 42 and the inter-electrode current flowing between the third electrode 43 and the fourth electrode 44. In this map, it is shown that the larger the difference of the inter-electrode current, the higher the concentration of $SO_X$ in the measured gas. By using the above method to calculate the $SO_X$ concentration, before the measured gas reaches the first electrochemical cell 51, the oxygen in the measured gas is removed at the third electrochemical cell 53 and the effect of the inter-electrode current generated by the decomposition of water is reduced, so it is possible to further improve the precision of detection of the $SO_X$ concentration at the first electrochemical cell 51. Note that, at step S109, in addition to the first electrochemical cell 51, the voltages applied to the second electrochemical cell 52 and the third electrochemical cell 53 may be made zero or reduced.

Further, in the tenth embodiment, as the control routine of water concentration stability judgment processing, any one of the control routines shown in FIG. 6 to FIG. 12 and FIG. 14 is performed. Furthermore, several of the control routines shown in FIG. 6 to FIG. 12 and FIG. 14 may be combined. Note that, when using a $SO_X$ detection system 1*c* to calculate the $SO_X$ concentration, instead of the air-fuel ratio sensor 104, the exhaust air-fuel ratio may be detected by the third electrochemical cell 53.

Above, preferred embodiments according to the present invention were explained, but the present invention is not limited to these embodiments and may be modified and changed in various ways within the scope of the claims. For example, the internal combustion engine in which the $SO_X$ detection system is used may be a spark ignition type internal combustion engine where spark plugs are arranged in the combustion chambers. Further, the above-mentioned embodiments can be freely combined and worked. For example, as the control routine of water concentration stability judgment processing using the $SO_X$ detection system 1, several of the control routines shown in FIG. 6 to FIG. 12 may be combined.

Note that the detectors used for detecting the various parameters in the different control routines can be said to be component elements of the $SO_X$ detection system. For example, the $SO_X$ detection system according to the first embodiment can be said to comprise the humidity sensor 103, since at step S201 of FIG. 6, the humidity of the intake air is detected by the humidity sensor 103.

What is claimed is:

1. A sulfur oxides detection system comprising:
   a device part arranged in an exhaust passage of an internal combustion engine and comprising a first electrochemical cell having a first solid electrolyte layer having oxide ion conductivity, a first electrode arranged on one surface of the first solid electrolyte layer so as to be exposed to gas to be measured, and a second electrode arranged on an other surface of the first solid electrolyte layer so as to be exposed to the atmospheric air, and a diffusion regulating layer to regulate diffusion of the gas to be measured;
   a power supply to supply voltage across the first electrode and the second electrode;
   a detector to detect a first current correlation parameter correlated with a current flowing between the first electrode and the second electrode; and an electronic control part to control the power supply and to acquire the first current correlation parameter from the detector, wherein the electronic control part is to control the power supply so that a first voltage which is a decomposition start voltage of water and sulfur oxides or greater is to be applied across the first electrode and the second electrode and to calculate a concentration of sulfur oxides in the gas to be measured based on the first current correlation parameter detected by the detector if the first voltage is applied across the first electrode and the second electrode and the electronic control part is to judge whether a concentration of water in the gas to be measured is stable and does not calculate the concentration of sulfur oxides in the gas to be measured if the electronic control part judges that the concentration of water in the gas to be measured is not stable.

2. The sulfur oxides detection system according to claim 1, wherein the device part further comprises a second electrochemical cell having a second solid electrolyte layer having oxide ion conductivity, a third electrode arranged on one surface of the second solid electrolyte layer so as to be exposed to the gas to be measured, and a fourth electrode arranged on an other surface of the second solid electrolyte layer so as to be exposed to the atmospheric air, the power supply is to apply voltage across the third electrode and the fourth electrode and the detector is to detect a second current correlation parameter correlated with a current flowing between the third electrode and the fourth electrode, and the electronic control part is also to control the power supply so that a second voltage which is a decomposition start voltage of water or greater is applied across the third electrode and the fourth electrode and is to judge that the concentration of water in the gas to be measured is not stable if an amount of change of the second current correlation parameter detected by the detector is a predetermined value or greater if the second voltage is applied across the third electrode and the fourth electrode.

3. The sulfur oxides detection system according to claim 1, wherein the electronic control part is also to control the power supply so that a second voltage which is a decomposition start voltage of water or greater is applied across the first electrode and the second electrode and is to judge that the concentration of water in the gas to be measured is not stable if an amount of change of the first current correlation parameter detected by the detector is a predetermined value or greater if the second voltage is applied across the first electrode and the second electrode.

4. The sulfur oxides detection system according to claim 1, wherein the sulfur oxides detection system further comprises a humidity sensor arranged in an intake passage of the internal combustion engine, and the electronic control part is also to judge that the concentration of water in the gas to be measured is not stable if an amount of change of humidity of the intake air detected by the humidity sensor is a predetermined value or greater.

5. The sulfur oxides detection system according to claim 1, wherein the electronic control part is also to judge that the concentration of water in the gas to be measured is not stable if it judges that a type of fuel fed to a combustion chamber of the internal combustion engine has been switched.

6. The sulfur oxides detection system according to claim 5, wherein the system further comprises an ethanol concentration sensor arranged in a feed path of the type of fuel fed to the combustion chamber, and the electronic control part is also to judge that the type of fuel has been switched if an amount of change of the concentration of ethanol in the fuel detected by the ethanol concentration sensor is a predetermined value or greater.

7. The sulfur oxides detection system according to claim 5, wherein the system further comprises an air-fuel ratio sensor arranged in the exhaust passage, and the electronic control part is also to control a fuel amount fed to the combustion chamber by feedback so that the air-fuel ratio detected by the air-fuel ratio sensor becomes a target air-fuel ratio, and is to judge that the type of fuel has been switched if the target air-fuel ratio is maintained constant and an amount of change of the ratio between an amount of the intake air fed to the combustion chamber and the fuel amount fed to the combustion chamber is a predetermined value or greater.

8. The sulfur oxides detection system according to claim 5, wherein the electronic control part is also to judge that the type of fuel has been switched in the period from when a fuel tank of the internal combustion engine is filled with fuel to when a predetermined amount or greater of fuel is fed to the combustion chamber.

9. The sulfur oxides detection system according to claim 1, wherein the electronic control part is also to judge that the concentration of water in the gas to be measured is not stable if judging that there is condensed water at least at one of an exhaust gas recirculation (EGR) passage connecting the intake passage of the internal combustion engine with the exhaust passage and the exhaust passage or that condensed water will be formed at least at one of the EGR passage and the exhaust passage.

10. The sulfur oxides detection system according to claim 1, wherein the electronic control part is also to judge that the concentration of water in the gas to be measured is not stable in the period from when water or an aqueous solution is injected into a path by which the gas to be measured reaches the device part to when the electronic control part judges that the injected water or aqueous solution passes the device part in the exhaust passage.

11. The sulfur oxides detection system according to claim 1, wherein the electronic control part is also to calculate the concentration of sulfur oxides in the gas to be measured if judging that an exhaust air-fuel ratio of exhaust gas discharged from a combustion chamber of the internal combustion engine is stable and that the concentration of water in the gas to be measured is stable.

* * * * *